United States Patent [19]
Suzuki

[11] Patent Number: 5,801,763
[45] Date of Patent: Sep. 1, 1998

[54] FACE IMAGE TAKING DEVICE

[75] Inventor: Hiroyoshi Suzuki, Tokyo, Japan

[73] Assignee: Mitsubishi Denki Kabushiki Kaisha, Tokyo, Japan

[21] Appl. No.: 575,487

[22] Filed: Dec. 20, 1995

[30] Foreign Application Priority Data

Jul. 6, 1995 [JP] Japan .................. 7-170977

[51] Int. Cl.⁶ .................................. H04N 7/18
[52] U.S. Cl. .................. 348/77; 340/439; 340/575; 340/576; 348/342
[58] Field of Search .................. 348/15, 77, 409, 348/439; 382/103, 118, 128; 340/439, 575, 576; H04N 7/18

[56] References Cited

U.S. PATENT DOCUMENTS

| | | | |
|---|---|---|---|
| 4,768,088 | 8/1988 | Ando | 348/77 |
| 5,012,522 | 4/1991 | Lambert | 382/118 |
| 5,280,530 | 1/1994 | Trew et al. | 382/103 |
| 5,293,427 | 3/1994 | Ueno et al. | 382/103 |
| 5,420,638 | 5/1995 | Riglet et al. | 348/409 |
| 5,438,357 | 8/1995 | McNelley | 348/15 |
| 5,500,671 | 3/1996 | Andersson et al. | 348/15 |
| 5,521,580 | 5/1996 | Kaneko et al. | 340/439 |
| 5,598,145 | 1/1997 | Shimotani et al. | 340/576 |
| 5,604,818 | 2/1997 | Saitou et al. | 382/128 |

FOREIGN PATENT DOCUMENTS

| | | |
|---|---|---|
| 4441332 | 5/1995 | Germany . |
| 9509689 | 9/1995 | Germany . |
| 9613614 | 11/1996 | Germany . |
| 468500 | 3/1992 | Japan . |
| 32154 | 2/1994 | Japan . |
| 632154 | 2/1994 | Japan . |
| 17772 | 3/1994 | Japan . |

*Primary Examiner*—Howard Britton
*Attorney, Agent, or Firm*—Sughrue, Mion, Zinn, Macpeak & Seas, PLLC

[57] ABSTRACT

A face image taking device including a two-dimensional image taker for taking an image of a predetermined region including a face of a person to be detected; an optical filter having a pass band passing at least an infrared ray in a predetermined wavelength region and arranged on an optical axis of the two-dimensional image taking; an eye detector for detecting eyes of the person to be detected based on the image of the face of the person to be detected which has been taken by the two-dimensional image taker; an infrared ray illuminator for illuminating at least the face of the person to be detected by an infrared ray which has passed through the optical filter, said infrared ray illuminator being arranged such that an angle made by the optical axis of the two-dimensional image taker and an optical axis of the infrared ray is a predetermined angle or more; and an exciting means for exciting the infrared ray illuminator when the eye detector does not detect the eyes of the person to be detected.

24 Claims, 23 Drawing Sheets

SUMY : Y-DIRECTION PIXEL SUMMATION VALUE
SUMX : X-DIRECTION PIXEL SUMMATION VALUE

FIGURE 7

```
          ┌─────────────────┐
          │ EYE EXTRACTION  │
          └────────┬────────┘
                   ▼
          ┌─────────────────────┐
          │ DETECT FACE GRAVITY │──ST301
          │ CENTER              │
          └──────────┬──────────┘
                     ▼
          ┌─────────────────────┐
          │ SET CANDIDATE       │──ST302
          │ EXISTING REGION     │
          └──────────┬──────────┘
                     ▼
          ┌─────────────────────┐
          │ FORM HISTOGRAMS IN  │
          │ CANDIDATE EXISTING  │──ST303
          │ REGIONS             │
          └──────────┬──────────┘
                     ▼
          ┌─────────────────────┐
          │ FORM HISTOGRAMS IN  │──ST304
          │ CANDIDATE REGION    │
          │ BANDS               │
          └──────────┬──────────┘
                     ▼
          ┌─────────────────────┐
          │ SET CANDIDATE       │──ST305
          │ REGIONS             │
          └──────────┬──────────┘
                     ▼
          ┌─────────────────────┐
          │ CALCULATE EYE       │──ST306
          │ EVALUATION FUNCTION │
          └──────────┬──────────┘
ST309                ▼             ST307
┌───────────┐    ◇ CANDIDATE ◇    YES
│ INCREMENT │◄── REGIONS     ─────────┐
│ CANDIDATE │    FINISHED?            │
│ REGION    │        │ NO             │
└─────┬─────┘        ▼   ST308        │
      │         ◇ EVALUATION ◇        │
      │  NO      FUNCTION             │
      └─────── DESIGNATES             │
                EYE?                  │
                    │ YES   ST310     │
                    ▼                 │
               ◇ LOCATION ◇  NO       │
                 LOWEST?  ────────────┤
                    │ YES             │
  ST311             ▼           ST312 ▼
┌──────────────┐          ┌──────────────┐
│ EYE DETECTION│          │ EYE DETECTION│
│ FLAG ON      │          │ FLAG OFF     │
└──────┬───────┘          └──────┬───────┘
       │      ┌────────┐         │
       └─────►│ RETURN │◄────────┘
              └────────┘
```

1

FACE IMAGE TAKING DEVICE

BACKGROUND OF THE INVENTION

1. Field of the Invention

The present invention relates to a device for taking an image of a face of a person, particularly to a face image taking device used in a person's state detecting device which detects a state of a person to be detected from a state of a characteristic region of the image of the face by image-processing the face image of the person to be detected.

2. Discussion of the Background

Conventionally, there has been disclosed a driver's state detecting device for photographing a face of a driver by a camera provided inside of a vehicle, extracting eyes which are a characteristic point of the face by processing a photographed image of the face and detecting a driving state of the vehicle driver such as looking aside or dozing while driving etc. from an opening/closing state of the eye, as shown in Japanese Unexamined Patent Publication No. 68500/1992 or Japanese Unexamined Patent Publication No. 32154/1994. As such a device for taking an image of a driver, there have been disclosed cameras which photograph the face of the driver by image taking elements such as CCD attached with a filter cutting a visible light in front thereof while illuminating the face of the driver by an infrared ray stroboscope or a LED having a wavelength region of near infrared ray which is arranged proximate to the camera.

FIG. 25 to FIG. 28 show such a conventional example wherein FIG. 25 is a structural view of a driver's state detecting device including a conventional face image taking device, FIG. 26 illustrates characteristic diagrams of spectroscopic reflectances of various spectacle lenses, FIG. 27 shows a characteristic diagram of a spectroscopic transmittance of a visible light cut filter used in the face image taking device and FIG. 28 illustrates an example of an image of a face wearing spectacles in a bright state that is photographed by the conventional face image taking device. An explanation will be given of the conventional example as follows in reference to the above-mentioned drawings.

In FIG. 25, numeral 100 designates a face image taking unit and numeral 101 designates a two-dimensional image taking element which is constituted by CCDs in this example. Numeral 102 designates an image signal processing circuit, numeral 103 designates an image taking lens and numeral 104 designates a visible light cut filter arranged on an optical axis in front of the image taking lens 103. In the visible light cut filter of this example the wavelength at the transmittance of 50% is 700 nm and the filter cuts light having a wavelength that is substantially equal to or less than 700 nm.

The above-mentioned CCD 101, the image signal processing circuit 102, the image taking lens 103 and the visible light cut filter 104 constitute a camera unit 110. Numeral 105 designates an illumination control circuit to which a brightness/darkness output of the image signal processing circuit 102 is connected and numeral 106 designates a light source that is a near infrared ray light source and wherein a visible light cut filter is provided in front a light source in which a number of infrared ray LEDs having a high brightness is arranged, a halogen lamp or a xenon lamp. The illumination control circuit 105 and the near infrared ray light source 106 are integrated and are arranged separately from the camera unit 110. Numeral 120 designates a face image processing unit wherein numeral 121 designates an input interface (I/F) to which CCD photograph timing signals from the image signal processing circuit 102 are connected, numeral 122 designates an analog to the digital (A/D) converter to which an image output from the image signal processing circuit 102 is connected, numeral 123 designates an image processing hardware (H/W) including gate arrays or digital signal processors (DSP) to which an output from the A/D converter 122 is connected, numeral 124 designates an image memory connected to the image processing H/W, numeral 125 designates a CPU, numeral 126 designates a ROM, numeral 127 designates a RAM and numeral 128 designates an output interface (I/F). The A/D converter 122, the image processing H/W 123, the image memory 124, the ROM 126, the RAM 127 and the output I/F 128 are connected to the CPU 125 via a bus 129. Numeral 130 designates a driver and numeral 131 designates spectacles worn by the driver.

An explanation will be given of the operation as follows. A visible light component of 700 nm or less of a reflected light which is produced by reflecting illuminating light or external light by the face of the driver 130, is cut by the visible light cut filter 104, light in a near infrared region is condensed by the image taking lens 103 and the face image of the driver 130 is formed on the CCD 101 controlled by the image signal processing circuit 102. The image signal processing circuit 102 outputs the face image of the driver 130 formed on the CCD 101 to the A/D converter 122 as an image signal and at the same time, outputs a bright/dark state signal to the illumination control circuit 105 by calculating a brightness at the surrounding of the face of the driver 130 by calculating an average brightness on the CCD 101.

Here, the photographing of the driver 130 becomes difficult in a state where there is no illumination by solar ray as in the nighttime or in a tunnel. Accordingly, the illumination control circuit 105 turns on the near infrared ray light source 106 and illuminates the face of the driver 130 when a dark state signal is outputted from the image signal processing circuit 102.

Further, the face is photographed sufficiently brightly by a near infrared ray component of solar ray in the daytime. Accordingly, the illumination control circuit 105 turns off the near infrared light source 106 when a bright signal is outputted from the image signal processing circuit 102.

An image signal of the face image of the driver 103 is A/D-converted by the A/D converter 122 into a digital gradation image which is converted into a binarized image by the image processing.H/W 123 after eliminating small noise components by passing through a smoothing filter and is stored in the image memory 124. Next, access is made to the binary image in the image memory 124 by partly using the image processing H/W and eyes are extracted from the binarized image, the opening or closing state of the eyes is detected, the dozing state of the driver 130 is determined from the opening/closing state of the eyes and an alarm signal is sent from the output I/F 128 to the outside and alarms the driver 130 in case where the dozing state is determined. These series of operations are controlled by CPU 125 in compliance with orders stored in the ROM 126 in accordance with the CCD photograph timing signals and RAM 127 is used for storing temporary data in control and calculation.

However, there is a problem in such a conventional device in which the eyes of the driver wearing the spectacles 131 in the daytime cannot be photographed due to a reflection by lenses of the spectacles 131.

FIG. 26 shows examples of spectroscopic reflectance characteristics of a glass lens and a plastic lens of spectacles. In almost all the spectacles 131 in recent times, the surface of the lens of the spectacle is coated by a reflection preventive coating. The spectroscopic reflectance of such a coated spectacle lens is rapidly increased in the near infrared region as illustrated in comparison with a case of a non-coated lens. In running a vehicle the driver 130 normally drives while looking slightly upwardly. In such a case, white cloud or a portion of outside scenery is reflected by the spectacles 131 of the driver 130 and the eyes in the face image of the driver 130 photographed by the conventional image taking device 100 is difficult to see even with the non-coated spectacles. Especially in case of the coated spectacles the eyes cannot be seen at all by the surface reflection of the lenses of the spectacles as illustrated in FIG. 28 due to the high spectroscopic reflectance of the spectacle lenses in the near infrared region.

Therefore, the conventional device has a drawback in which the dozing or side looking of the driver cannot be detected.

SUMMARY OF THE INVENTION

It is an object of the present invention to resolve the above problems and to provide a face image taking device capable of taking an image of a face of a driver while restraining influence of a surface reflection light by lenses of spectacles to the utmost even if the driver wears the spectacles.

Further, it is an object of the present invention to provide a face image taking device reducing hour average power consumption and maintaining a long life of the device.

According to a first aspect of the present invention, there is provided a face image taking device comprising:

a two-dimensional image taking means for taking an image of a predetermined region including a face of a person to be detected;

an optical filter having a pass band passing at least an infrared ray in a predetermined wavelength region and arranged on an optical axis of the two-dimensional image taking means;

an eye detecting means for detecting eyes of the person to be detected based on the image of the face of the person to be detected which has been taken by the two-dimensional image taking means;

an infrared ray illuminating means for illuminating at least the face of the person to be detected by an infrared ray which has passed through the optical filter, said infrared ray illuminating means being arranged such that an angle made by the optical axis of the two-dimensional image taking means and an optical axis of the infrared ray is a predetermined angle or more; and an exciting means for exciting the infrared ray illuminating means when the eye detecting means does not detect the eyes of the person to be detected.

According to a second aspect of the present invention, there is provided a face image taking device according to the first aspect, further comprising a brightness/darkness detecting means for detecting either one of a bright state and a dark state at a surrounding of the person to be detected or at a vicinity of the face by detecting a brightness of the surrounding of the person to be detected or the vicinity of the face; and wherein the exciting means excites the infrared ray illuminating means in case where the brightness/darkness detecting means detects the bright state and the eye detecting means does not detect the eyes of the person to be detected.

According to a third aspect of the present invention, there is provided a face image taking device according to the second aspect, wherein the brightness/darkness detecting means determines either one of the bright state and the dark state based on whether a brightness of an image including the face of the person to be detected which has been taken by the two-dimensional image taking means is a predetermined brightness or more.

According to a fourth aspect of the present invention, there is provided a face image taking device according to the first aspect, wherein the exciting means once stops the infrared ray illuminating means when a predetermined period of time has elapsed since the infrared ray illuminating means was excited.

According to a fifth aspect of the present invention, there is provided a face image taking device according to the first aspect, further comprising a spectacle detecting means for detecting presence or absence of spectacles worn by the person to be detected; and wherein the exciting means excites the infrared ray illuminating means in case where the spectacle detecting means detects spectacles and the eye detecting means does not detect the eyes of the person to be detected.

According to a sixth aspect of the present invention, there is provided a face image taking device according to the second aspect, further comprising a second infrared ray illuminating means for the dark state for illuminating the face of the person to be detected by an infrared ray which has passed through the optical filter when the brightness/darkness detecting means detects the dark state, said second infrared ray illuminating means for the dark state being provided separately from the infrared ray illuminating means excited when the eye detecting means does not detect the eyes of the person to be detected.

According to a seventh aspect of the present invention, there is provided a face image taking device comprising:

a two-dimensional image taking means for taking an image of a predetermined region including a face of a person to be detected; and an optical filter having a first pass band passing a visible light in a predetermined wavelength range and a second pass band passing an infrared ray having a predetermined wavelength or more and arranged on an optical axis of the two-dimensional image taking means.

According to an eighth aspect of the present invention, there is provided a face image taking device according to the seventh aspect, wherein the second pass band of the optical filter passes only an infrared ray in a predetermined wavelength range.

According to a ninth aspect of the present invention, there is provided a face image taking device comprising:

a two-dimensional image taking means for taking an image of a predetermined region including a face of a person to be detected;

an optical filter having a first pass band passing a visible light in a predetermined wavelength range and a second pass band passing an infrared ray having a predetermined wavelength or more and arranged on an optical axis of the two-dimensional image taking means;

an eye detecting means for detecting eyes of a person to be detected based on an image of the face of the person to be detected which has been taken by the two-dimensional image taking means;

an infrared ray illuminating means for illuminating at least the face of the person to be detected by an infrared ray which has passed through the optical filter, said infrared ray illuminating means being arranged such that an angle made by an optical axis of the two-dimensional image taking means and an optical axis of the infrared ray is a predetermined angle or more; and an exciting means for exciting the infrared ray illuminating means when the eye detecting means does not detect the eyes of the person to be detected.

According to a tenth aspect of the present invention, there is provided a face image taking device according to the seventh or ninth aspect, further comprising a first optical filter having a first pass band and a second optical filter having a second pass band both constituting the optical filter;

a brightness/darkness detecting means for detecting either one of a bright state and a dark state at a surrounding of the person to be detected or at a vicinity of the face by detecting a brightness of the surrounding of the person to be detected or the vicinity of the face; and a filter interchanging means for disposing the first optical filter on an optical axis of the two-dimensional image taking means when the brightness/darkness detecting means detects the bright state and disposing the second optical filter on the optical axis of the two-dimensional image taking means when the brightness/darkness detecting means detects the dark state.

According to the first aspect of the face image taking device the face of the person to be detected is illuminated by exciting the infrared ray illuminating means when the eye detecting means does not detect the eyes of the person to be detected.

According to the second aspect of the face image taking device the face of the person to be detected is illuminated by exciting the infrared ray illuminating means in case where the brightness/darkness detecting means detects the bright state and the eye detecting means does not detect the eyes of the person to be detected.

According to the third aspect of the face image taking device the device determines the bright state or the dark state based on whether the brightness of the image including the face of the person to be detected which has been taken by the two-dimensional image taking means is the predetermined brightness or more.

According to the fourth aspect of the present invention the infrared ray illuminating means is once stopped when the predetermined time has elapsed since the infrared ray illuminating means was excited.

According to the fifth aspect of the present invention the face of the person to be detected is illuminated by exciting the infrared ray illuminating means in case where the spectacle detecting means detects the spectacles and the eye detecting means does not detect the eyes of the person to be detected.

According to the sixth aspect of the present invention the device is provided with the second infrared ray illuminating means for the dark state which illuminates the face of the person to be detected by the infrared ray which has passed through the optical filter when the brightness/darkness detecting means detects the dark state and the second infrared ray illuminating means and the infrared ray illuminating means excited when the eye detecting means does not detect the eyes of the person to be detected function separately.

According to the seventh aspect of the face image taking device the image of the person to be detected is taken by passing the visible light in the predetermined wavelength range and the infrared ray having the predetermined wavelength or more.

According to the eighth aspect of the face image taking device the image of the face of the person to be detected is taken only by the visible light in the predetermined wavelength region and the infrared ray in the predetermined wavelength region.

According to the ninth aspect of the face image taking device the image of the face of the person to be detected is taken by the visible light in the predetermined wavelength region and the infrared ray having the predetermined wavelength or more and the face of the person to be detected is illuminated by exciting the infrared ray illuminating means in case where the eyes cannot be detected in the image of the face.

According to the tenth aspect of the face image taking device the first optical filter is disposed on the optical axis of the two-dimensional image taking means when the brightness/darkness detecting means detects the bright state and the second optical filter is disposed on the optical axis of the two-dimensional image taking means when the brightness/darkness detecting means detects the dark state.

BRIEF DESCRIPTION OF THE DRAWINGS

FIG. 7 is a flowchart with regard to eye extraction;

DETAILED DESCRIPTION OF PREFERRED EMBODIMENTS

EMBODIMENT 1

Figure 1:
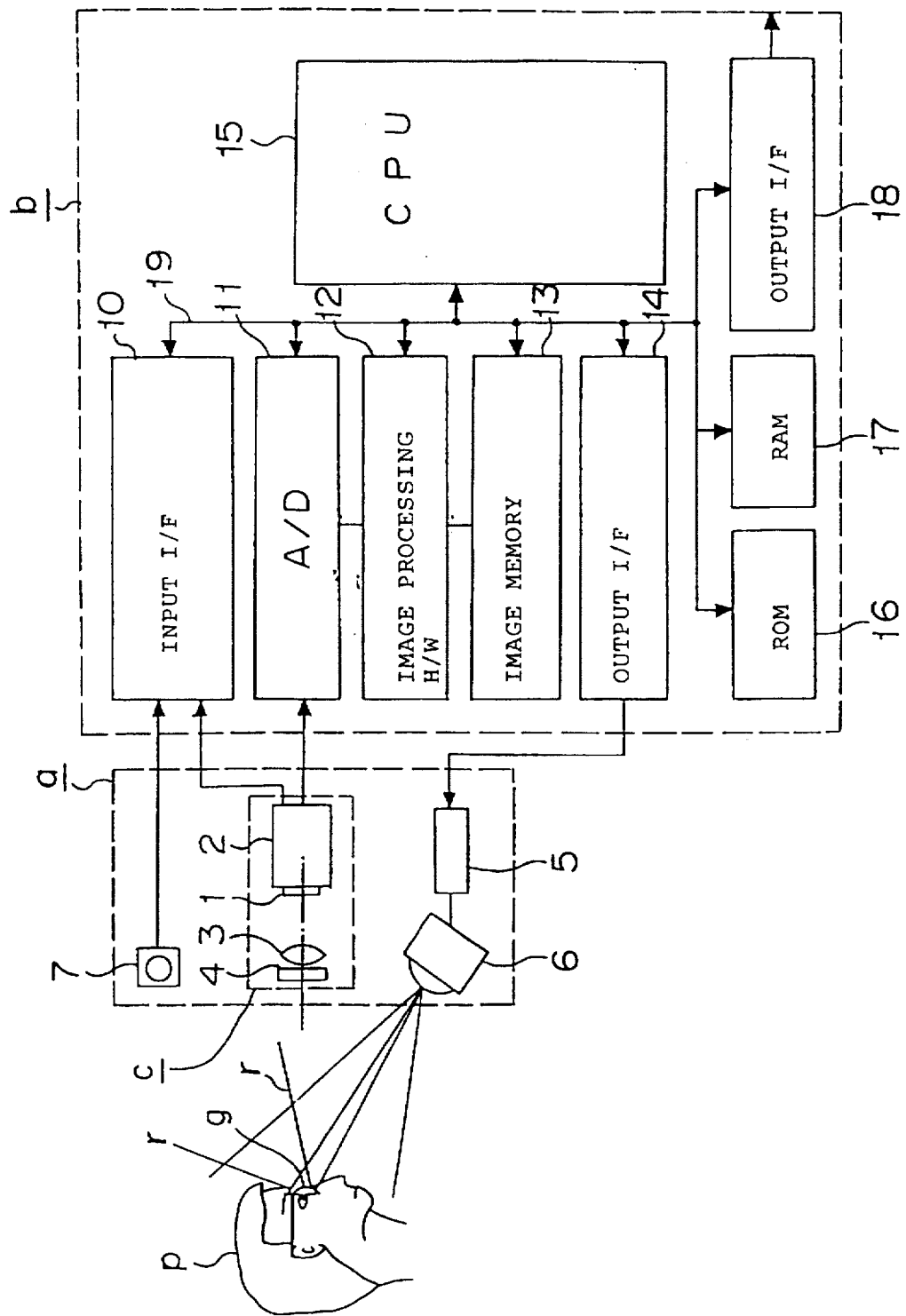
FIG. 1 is a structural view of a driver's state detecting device including a face image taking device of Embodiment 1.
Figure 2:
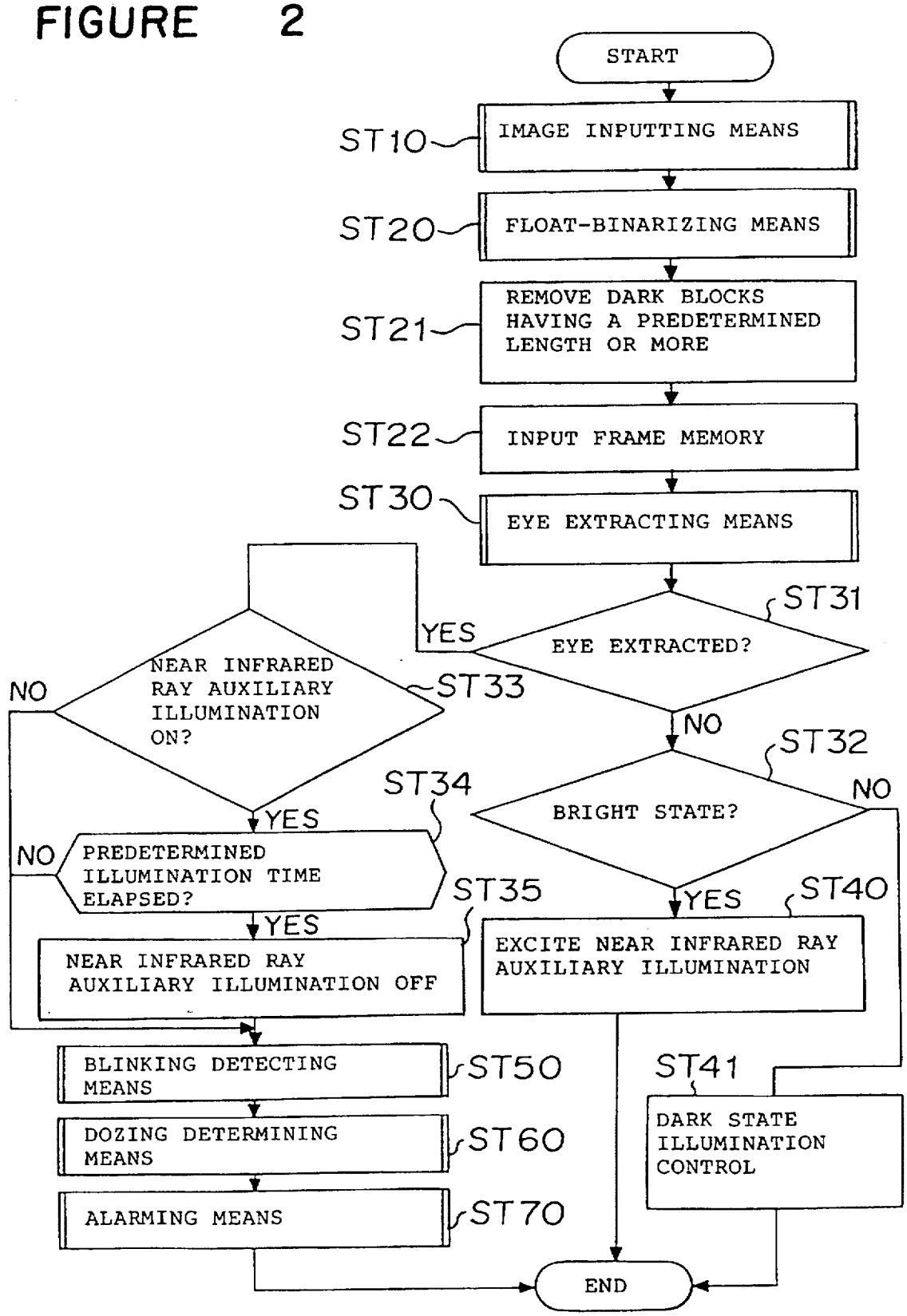
FIG. 2 is a flowchart for detecting a driver's state in Embodiment 1.
Figure 3:
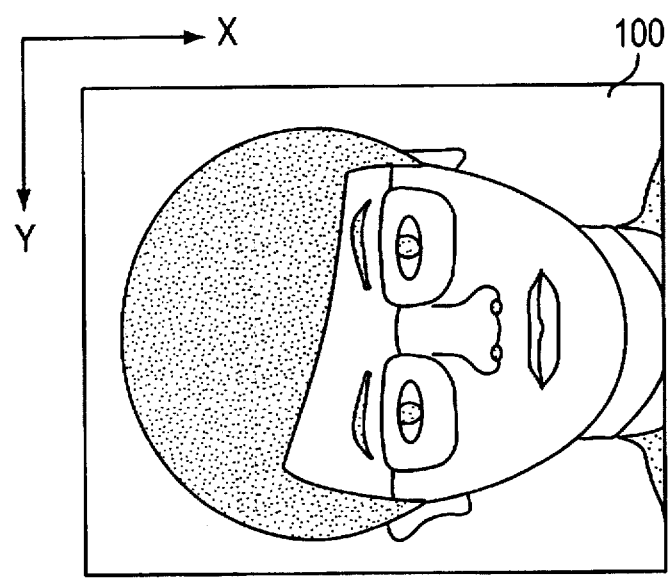
FIG. 3 is a schematic view of an image of a face of a driver wearing spectacles.
Figure 4:
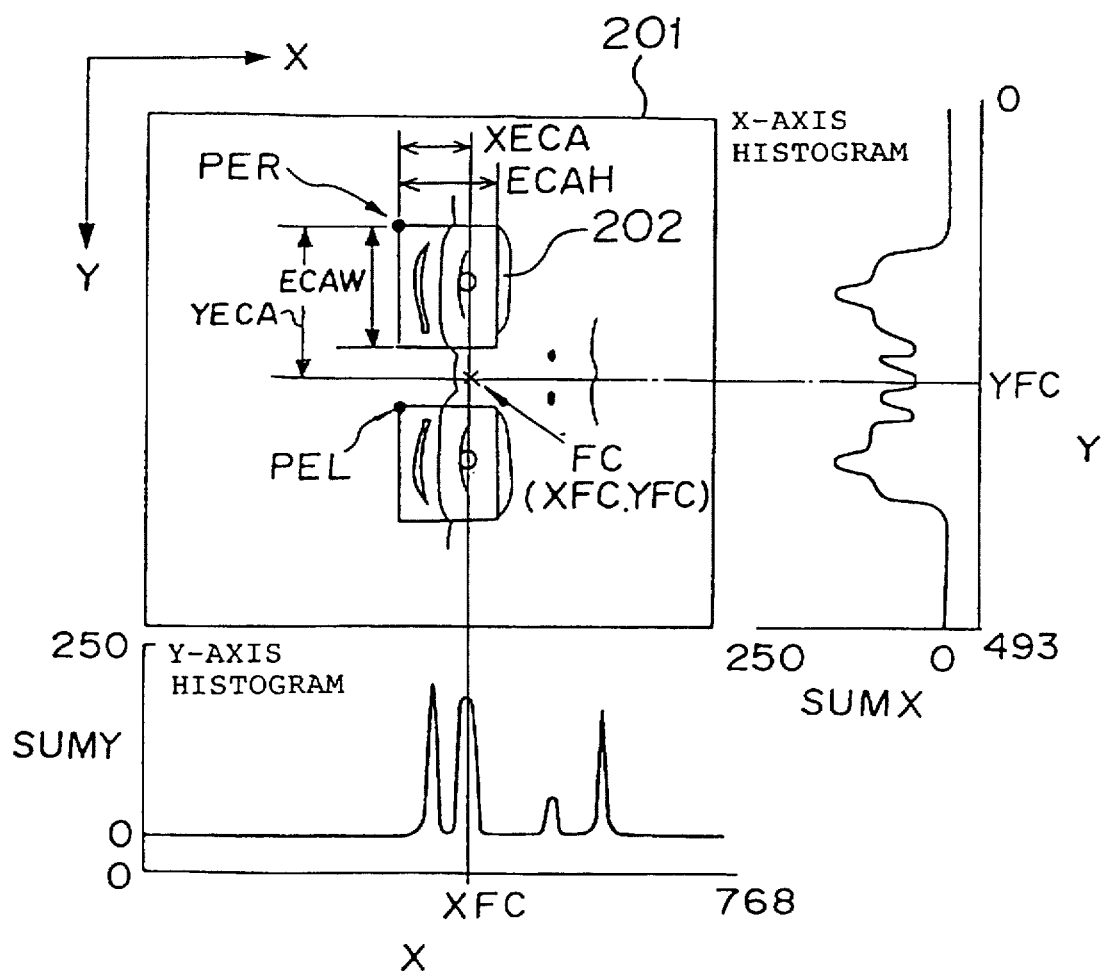
FIG. 4 is an explanatory view in setting eye existing regions.
Figure 5:
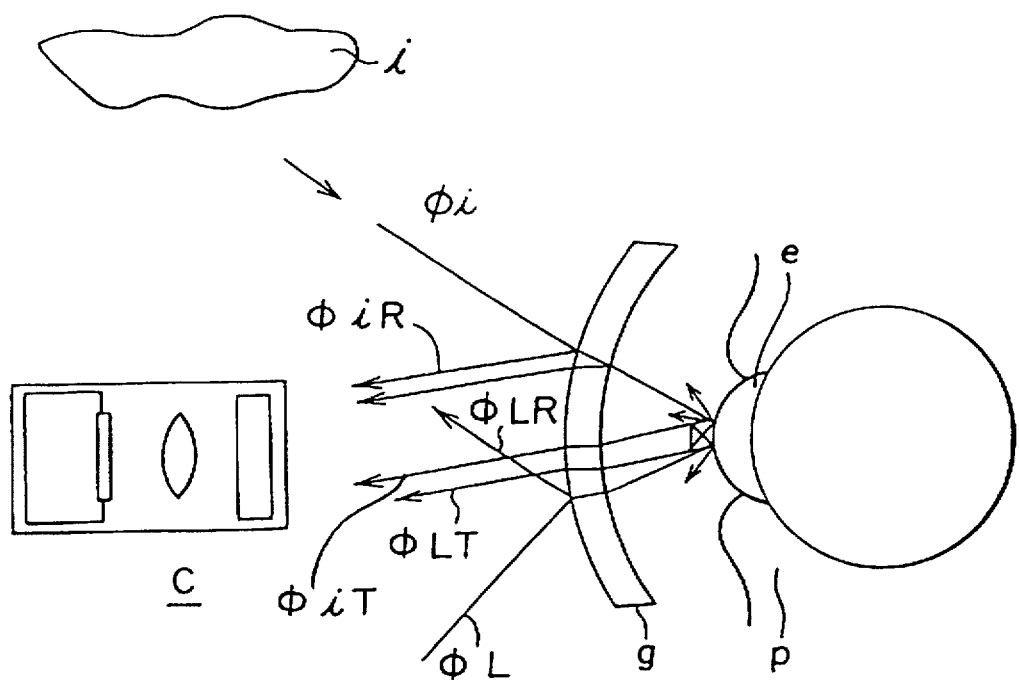
FIG. 5 is an explanatory view of light reflection at a face of a driver.
Figure 6:
FIG. 6 shows an example of an image of a face wearing spectacles in a bright state which is taken by the face image taking device of Embodiment 1.
Figure 8:
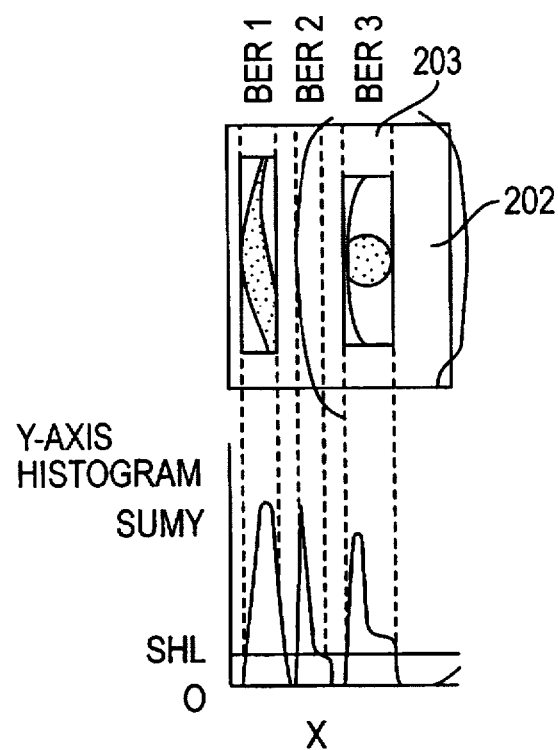
FIG. 8 shows a X-axis histogram of an eye existing region.
Figure 9:
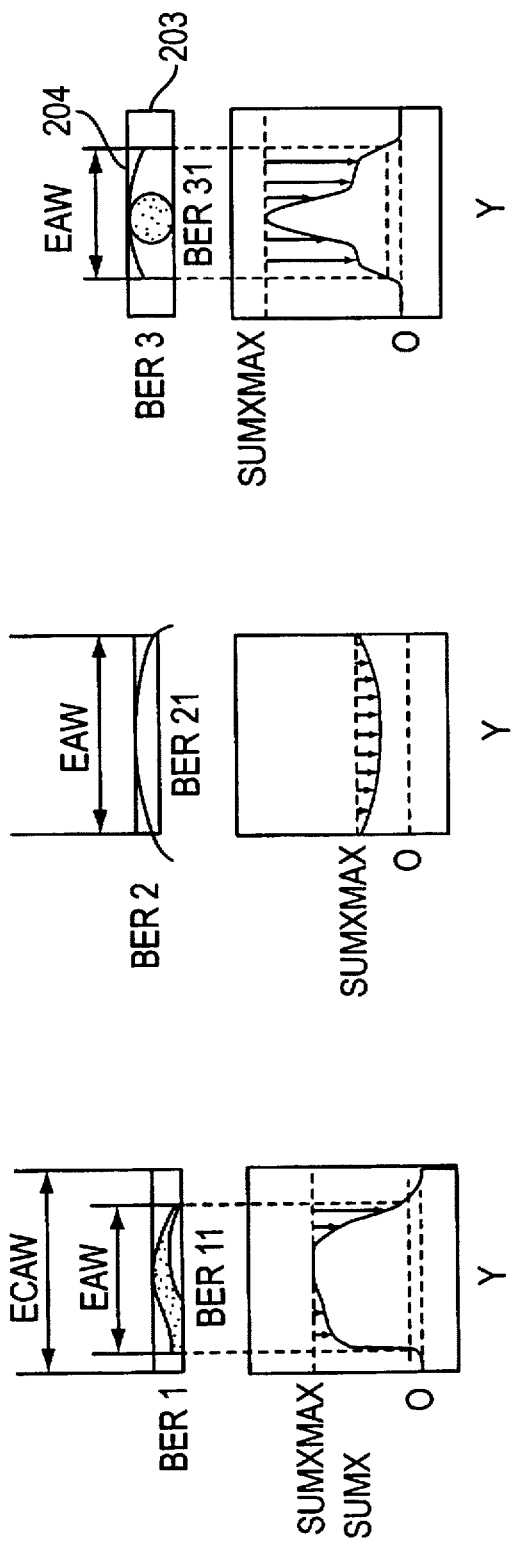
FIG. 9 shows X-axis histograms of candidate regions.

FIG. 1 through FIG. 9 show an embodiment of a face image taking device according to the present invention wherein FIG. 1 is a structural view of a driver's state detecting device including a face image taking device, FIG. 2 is a flowchart in detecting a driver's state, FIG. 3 is a schematic view of an image of a face of a driver wearing spectacles, FIG. 4 is an explanatory view in setting eye existing regions, FIG. 5 is an explanatory view of light reflection at a face of a driver, FIG. 6 shows an example of an image of a face wearing spectacles in a bright state which is taken by a face image taking device according to the present invention, FIG. 7 is a flowchart with regard to eye extraction, FIG. 8 illustrates a X-axis histogram of an eye existing region and FIG. 9 illustrates X-axis histograms of candidate regions. An explanation will be given of the embodiment in reference to the drawings as follows.

Figure 27:
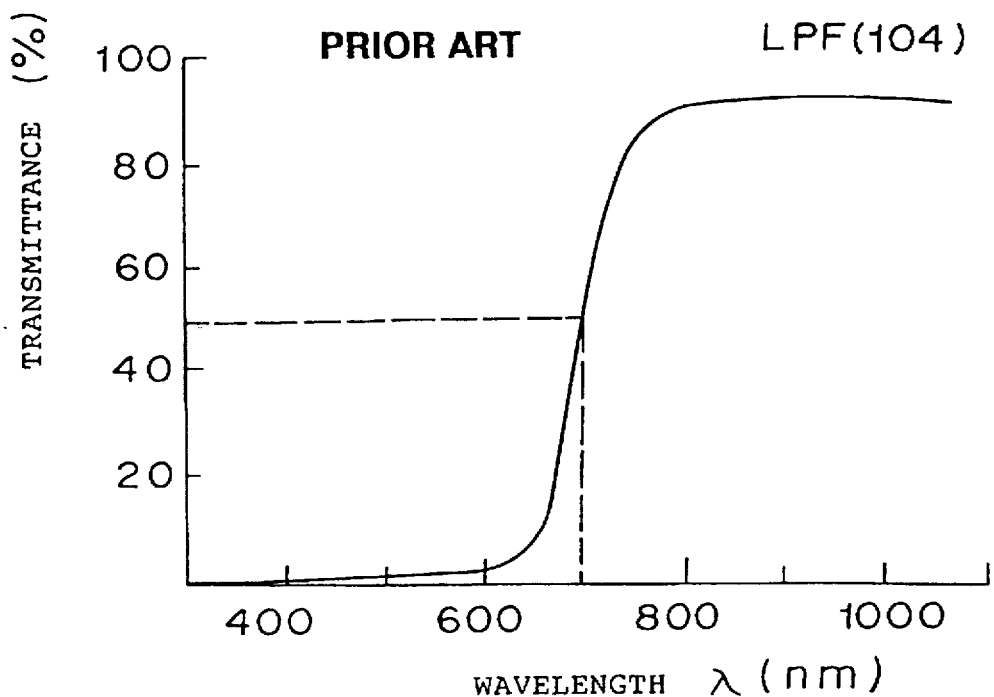
FIG. 27 is a characteristic diagram of a spectroscopic transmittance of a visible light cut filter used in the conventional face image taking device.

In FIG. 1 notation "a" designates a face image taking unit, notation "b" designates a face image processing unit and notation "c" designates a camera unit. In FIG. 1 numeral 1 designates a CCD as a two-dimensional image taking means for taking an image of a predetermined region including a face of a driver wherein pixels of 768×493 or a total of 380,000 are used. Numeral 2 designates an image signal processing circuit for processing signals from CCD 1 and numeral 3 designates an image taking lens provided on an optical axis in front of CCD 1 and numeral 4 designates a visible light cut filter as an optical filter for cutting a visible light incident on the image taking lens 3 which is provided on the optical axis in further front of the image taking lens 3. The visible light cut filter 4 has a spectroscopic characteristic as shown in FIG. 27. Further, the camera unit c constituted by CCD 1, the image signal processing circuit 2, the image taking lens 3 and the visible light cut filter 4, is arranged on a dashboard, an instrument panel etc. at a driver's seat which photographs a predetermined region including a face of the driver from in front of the driver towards a direction by which the face in its longitudinal direction corresponds to the 768 pixels of CCD 1. It is most advantageous for extracting eye regions to render the photographing angle directed in front of and from obliquely below toward a face.

Numeral 5 designates an illumination control circuit as an exciting means for exciting or stopping an infrared ray light source by receiving an output from a CPU, mentioned later.

Numeral 6 designates an infrared ray light source as an infrared ray illuminating means for irradiating an infrared ray in a direction toward the face of the driver or in a direction including the vicinity by being excited by the illumination control circuit 5. The infrared ray light source 6 is attached at a position whereby a regular reflection light "r" which is produced by reflecting the near infrared ray irradiated from the near infrared ray light source 6 by lenses of spectacles of the driver, is not directly incident on the image taking lens 3 of the camera unit c. More specifically, the near infrared ray light source 6 is disposed at a location displaced upward, downward, leftward or rightward from the camera unit c such that an angle made by the optical axis of the near infrared ray irradiated by the near infrared ray light source 6 and the optical axis of the camera unit c is approximately 20° through 30° or more.

Numeral 7 designates an illuminance sensor as a brightness/darkness detecting means for detecting a brightness of the surrounding or the face of the driver and detecting whether it is in a bright state or in a dark state, which is installed at a location such as a dashboard or a portion in the vehicle below a rear window or the like to detect the brightness at the surrounding or the face of the driver.

The face image processing unit b is constituted as follows. In FIG. 1, numeral 10 designates an input I/F receiving various signals such as CCD photograph timing signals or shutter signals of the image signal processing circuit 2 and receiving an output signal from the illuminance sensor 7, numeral 11 designates a A/D converter to which an image output from the image signal processing circuit 2 is connected, numeral 12 designates an image processing hardware (H/W) constituted by gate arrays or digital signal processors (DSP) to which an output from the A/D converter 11 is connected, numeral 13 designates an image memory connected to the image processing H/W 12 and numeral 14 designates an output I/F outputting orders from a CPU 15 performing calculation at least one of outputs of which is connected to the illumination control circuit 5.

Numeral 16 designates a ROM wherein various programs or numerical values are stored, numeral 17 designates a RAM temporarily storing and holding values during calculation and numeral 18 designates an output I/F which is connected to various instruments in later stages. Further, the input I/F 10, the A/D converter 11, the image processing H/W 12, the image memory 13, ROM 16, RAM 17 and the output I/F 18 are connected to CPU 15 by a bus 19.

FIG. 2 is a flowchart in detecting a state of a driver. Although there is a face image taking device controlling to turn on the near infrared ray light source in the dark state as in the nighttime, a detailed explanation thereof will be omitted in Embodiment 1.

Now, an explanation will be given of the operation of the Embodiment 1 in reference to FIG. 2. In an image inputting means of step ST10 an image signal VOUT of an original image shown in FIG. 3 which is taken by CCD 1 is converted into a digital gradation image signal which is outputted to the image processing H/W 12 where small noise components are eliminated by passing the signal through a suitable smoothing filter. In a float-binarizing means of step ST20 the signal is float-binarized into a binarized image by the image processing H/W 12, a length of a pixel that is a little larger than a width in the longitudinal direction of the eye is rendered a predetermined length. In step ST21 dark blocks each of which is larger than the predetermined length in the longitudinal direction of the face are removed. In step ST22 a binarized image 201 in which a hair region which is considerably different depending on individuals is substantially removed as shown in FIG. 4, is inputted and stored in the image memory 13. Next, in step ST30 an eye extracting means extracts eyes from the face image by making access to the binarized image 201 in the image memory 13 by partly using the image processing H/W 12. In step ST30 an eye extraction routine, mentioned later, is performed. When the above-mentioned eye extraction routine has been finished by the eye extracting means as an eye detecting means in step ST30, whether an eye extraction flag is ON or not is determined in step ST31.

Figure 28:
FIG. 28 shows an example of an image of a face wearing spectacles in a bright state which is taking by the conventional face image taking device.

Here, the eye detecting flag is OFF in a face image in which the eyes are not seen at all by the surface reflection of the spectacle lenses as shown in FIG. 28 since the eyes are not detected in the eye extraction routine ST30. When the eye detecting flag is OFF, the operation proceeds to step ST32 where the operation reads a brightness/darkness signal of the illuminance sensor 7 from the input I/F 10 and detects whether external environment is bright or not from the brightness/darkness signal. When the external environment is determined to be in the bright state, it is determined that the eyes are not extracted due to the surface reflection of the spectacle lenses and the operation controls to turn on the near infrared ray light source 6 by sending an illumination control signal for removing the spectacle reflection from the output I/F 14 to the illumination control circuit 5 in step ST40, by which the face of the driver or the vicinity including the face is illuminated.

Now, an explanation will be given of the reason for irradiating the near infrared ray to the face of the driver when the eyes cannot be detected by the surface reflection of the spectacle lenses.

FIG. 5 is a diagram explaining reflecting luminous fluxes and transmitting luminous fluxes at an eye "e" and a spectacle "g" in case where a luminous flux Φ from an external object "i" and a luminous flux ΦL from the near infrared ray light source 6 irradiate a face of a driver wearing the spectacle "g". In FIG. 5, a luminous flux Φ entering the camera unit c is expressed by the following equation (1).

$$\Phi = \Phi iR + \Phi iT + \Phi LT \quad (1)$$

where ΦiR is a reflecting luminous flux of the luminous flux Φi reflected by the spectacle g, ΦiT is a diffused reflecting luminous flux of the luminous flux Φi which is reflected by the eye e of a driver "p" after transmitting through the spectacle "g" and ΦLT is a similar diffused reflection luminous flux of a radiation luminous flux ΦL from the near infrared ray light source 6 reflected by the eye e.

As mentioned above the near infrared light source 6 is disposed such that the angle made by the optical axis of its irradiating light and the optical axis of the camera unit c is a predetermined angle or more and therefore, a reflection luminous flux ΦLR of the irradiation luminous flux ΦL from the near infrared ray light source 6 reflected by the lens of the spectacle g is not incident on the camera unit c.

When an image brightness on CCD 1 is described by classifying it in accordance with the reflecting luminous flux reflected by the spectacle g and the diffused reflecting luminous flux reflected by the eye e, a brightness ΦR owing to the reflecting luminous flux by the spectacle g and a brightness ΦT owing to the diffused reflecting luminous flux by the eye e are respectively expressed by the following equation (2).

$$\Phi R = \Sigma_\lambda \Phi iR(\lambda) F(\lambda) R(\lambda)$$

$$\Phi T = \Sigma_\lambda (\Phi iT(\lambda) + \Phi LT) F(\lambda) R(\lambda) \quad (2)$$

where F(λ) is a spectroscopic transmittance characteristic of the optical filter 4 and R(λ) is a spectroscopic sensitivity characteristics of CCD 1. A ratio K of the brightness ΦT owing to the diffused reflection luminous flux by the eye e as compared with total brightness of the image is given by the following equation (3).

$$K = \Phi T/(\Phi R + \Phi T) \quad (3)$$

Accordingly, the larger the ratio K, the more clearly the eye e can be observed.

Now, as is apparent from the equation (3), in case where the eye cannot be recognized since the ratio of the brightness ΦR owing to the reflecting luminous flux by the spectacle g as compared with the brightness ΦT is large, the ratio of ΦT to ΦR is increased by adding ΦLT by turning on the near infrared ray light source 6.

Accordingly, the eyes can distinctly by observed by adding the near infrared ray even if there is the reflection by the spectacle lenses.

FIG. 6 shows an image when the face of the driver p is illuminated by turning on the near infrared ray light source 6 in the state of the image in FIG. 28 wherein the eyes are not observed due to the surface reflection of the lenses of the spectacles g. As illustrated the eyes are distinctly observed by the illumination by the near infrared light source 6.

Further, the external environment is in the dark state when the determination in step ST32 is N. In this case the operation proceeds to step ST41 and performs an illumination control in the dark state.

Now, after exciting the near infrared light source 6 to remove the influence of the reflection by the spectacle g, the main routine returns to step ST10 and successively performs the above-mentioned processings. In step ST31 at the successive processing the determination is Y since the eyes are detected and proceeds to step ST33 this time.

The successive steps ST33 through ST35 is a processing for stopping the excited near infrared light source 6.

When the eyes cannot be detected, the near infrared light source 6 is excited in step ST40 by which the eyes can be detected irrespective of the reflection by the spectacle g. Meanwhile, the reflection by the spectacle g does not continue over a long period of time and disappears in a comparatively short period of time in accordance with a change in the environmental situation.

Accordingly, in steps ST33 through ST35 the illumination of the infrared ray is once stopped after a predetermined period of time since the near infrared ray light source 6 has been excited and when the eyes are detected in step ST31 in a successive processing it is determined that reflection of the spectacle g has been removed and the state of stopping the near infrared ray ray light source 6 is continued. When the eyes cannot be detected, it is determined that the reflection of the spectacle g continues and the near infrared ray light source 6 is again excited in step ST40 in the successive processing.

Specifically, when it is confirmed that the eye detection flag is ON in step ST31, whether the illumination for removing the spectacle reflection by the near infrared ray light source 6 is being performed or not is determined in step ST33. When the illumination for removing spectacle reflection is performed, an elapsed period of time of illumination is investigated in step ST34 and when a predetermined time period has elapsed, the illumination for removing the spectacle reflection is once turned off in step ST35. The predetermined time period may be several minutes or less considering the duration time period of the spectacle reflection. In this way the time of use of the near infrared ray light source 6 in the bright external environment can be minimized.

When the eyes of the driver can be detected as mentioned above, the state of the driver is detected based thereon.

In a blinking detecting means in step ST50 blinking of the driver p is detected by an opening/closing state of the extracted eye e of the driver p. In a dozing determining means in the successive step ST60 dozing is determined based on the state of blinking and an alarm is sent to the driver p to awake him by an alarming means in ST70 in accordance with the state of dozing.

Now, an explanation will be given of the eye extraction routine of the eye extracting means in step ST30.

In FIG. 7 a X-axis histogram SUMX and a Y-axis histogram SUMY of the image are calculated by summing up a binarized level of the binarized image 201 respectively in the X-axis direction and the Y-axis direction as shown in FIG. 4 in step ST301. Gravity center locations XFC and YFC of the respective histograms SUMY and SUMX are calculated and defined as face gravity center coordinates FC (XFC, YFC) and a light candidate existing region 202 having a X-axis direction length ECAH and a Y-axis direction length ECAY is set with a point PER displaced from the face gravity center FC by XECA in the X-axis direction and YECA in the Y-axis direction as a starting point in step ST302 and a left candidate existing region 202 having the same size is similarly set with a point PEL as a staring point.

Next, in step ST303 a Y-axis histogram SUMY in the candidate existing region 202 is calculated as shown in FIG. 8 and regions in each of which SUMY is a predetermined threshold SHL or more are determined as candidate region bands 203.

In FIG. 8 a region band BER1 corresponding to an eyebrow, a region band BER2 corresponding to a spectacle frame and a region band BER3 corresponding to an eye are registered as the candidate region bands 203. Incidentally, although one candidate existing region 202 is shown in FIG. 8, the other candidate existing region 202 is naturally processed in the similar way.

Further, in step ST304 X-axis histograms SUMX in the respective candidate region bands 203 are calculated as shown in FIG. 9 and regions in each of which SUMX is similarly a predetermined another threshold SHL or more are set as candidate regions 204. In FIG. 9 a region BER11 corresponding to the eyebrow, a region BER21 corresponding to the spectacle frame and a region BER31 corresponding to the eye are registered as the candidate regions 204. In step ST306 a maximum value SUMXMAX and a dispersion of a deviation from the maximum value (SUMXMAX −SUMX) etc. are calculated from the X-axis histogram SUMX of each of the registered candidate regions 204 whereby an eye evaluation function is calculated with respect to each of the candidate regions 204. As shown in FIG. 9 SUMX in the eye region has a characteristic wherein both the maximum value and the dispersion of the deviation are larger than those in the other regions.

Next, in step ST307 each of the candidate regions 204 is read one by one. In step ST308 whether the evaluation function is in a predetermined range showing the eye is determined. When one of the candidate regions 204 is not determined as the eye, the candidate region 204 is incremented in step ST309 and the similar operation is performed with regard to the successive candidate regions. When there is no candidate region 204 to be determined in step ST307, in step ST312 the eye detection flag is made OFF and the processing is made return to the main routine. When there are candidate regions 204 which are determined as the eye in step ST308, in step ST310 the lowest one of the candidate regions 204 determined as corresponding to the eye is identified as corresponding to the eye and the eye extraction routine is finished by making the eye detecting flag ON in step ST311.

As stated above according to the embodiment the eyes can easily be observed even in case where outside scenery or the like is reflected by the spectacle g worn by the operator p.

Further, it is not necessary to use the near infrared light source 6 in case where the outside scenery is not reflected by the spectacle g and therefore, the invention provides an advantage wherein the time of use of the near infrared ray light source 6 is restrained as less as possible whereby the hour average power consumption is reduced and the life of the near infrared light source 6 is prolonged.

EMBODIMENT 2

Although the case in which the illuminance sensor 7 is used as the brightness/darkness detecting means in the above-mentioned Embodiment 1, it is possible to determine the brightness/darkness without using the illuminance sensor 7. That is, it is possible to adopt a method of determining the brightness/darkness from the brightness in the vicinity of the driver p without using the brightness/darkness state of the external environment, in other word, a value corresponding to the brightness of the face image of the driver p.

Figure 10:
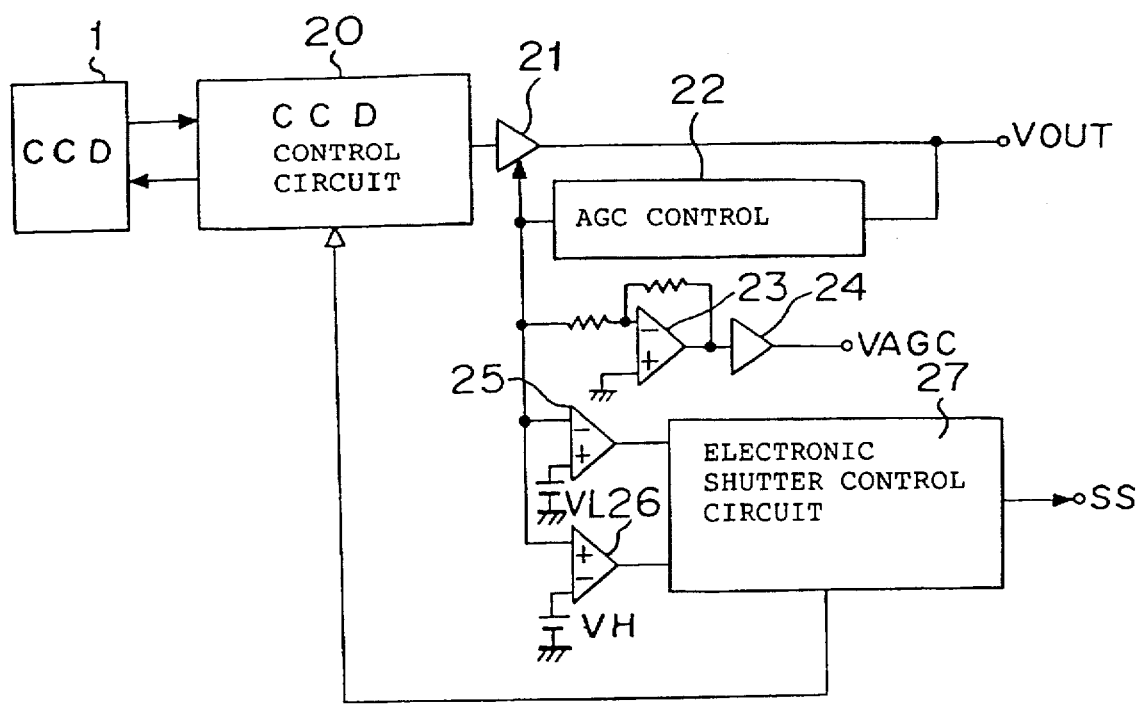
FIG. 10 is a block diagram of an image signal processing circuit.
Figure 11:
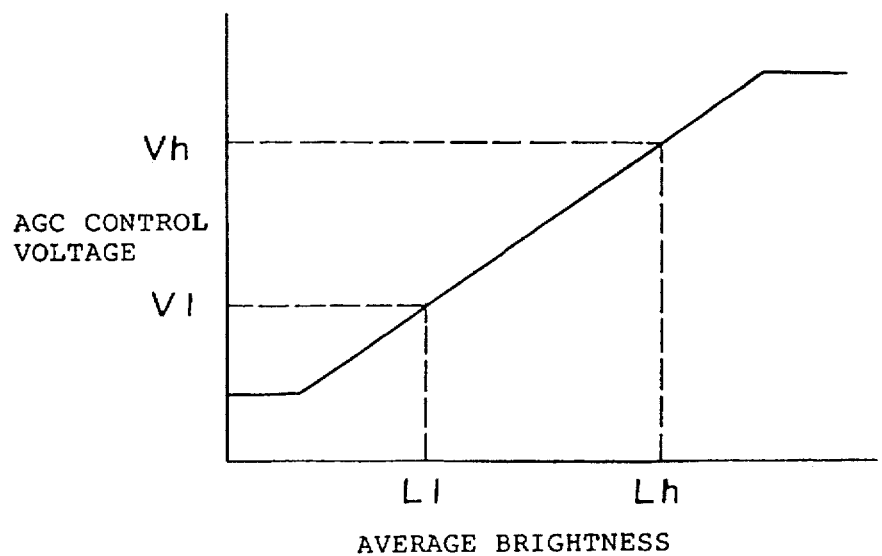
FIG. 11 is a control characteristic diagram of an automatic gain control circuit.

FIG. 10 is a block diagram of an image signal processing circuit 2 and FIG. 11 is a control characteristic diagram of an automatic gain control (AGC) circuit.

Firstly, an explanation will be given of the operation of the image signal processing circuit 2.

In FIG. 10 a CCD control circuit 20 controls photograph timings of CCD 1 and an image storing time (hereinafter, shutter time) and outputs the photographed image as an image signal VOUT. A AGC control circuit 22 calculates the image average brightness L by integrating an output of a gain variable amplifier 21 and controls the gain of the gain variable amplifier 21 such that a AGC control voltage VAGC becomes a predetermined target control voltage by feeding back the AGC control voltage VAGC corresponding to the image average brightness L as shown in FIG. 11 to the gain variable amplifier 21. The image signal VOUT in case where the image average brightness is controlled by the gain variable amplifier 21, is inputted to the A/D converter 11 of the face image processing unit b and is converted into a digital gradation image.

Meanwhile, the AGC control voltage VAGC is compared with a voltage Vl corresponding to a minimum brightness Ll and a voltage Vh corresponding to a maximum brightness Lh respectively shown in FIG. 11 at comparing circuits 25 and 26 and the respective results of comparison are inputted to an electronic shutter control circuit 27. When the image average brightness L of the face image of the driver p is changed exceeding the control range Vl through Vh specified by the AGC control circuit 22 when the brightness state of the external environment with regard to the vehicle such as the height and direction of the sun, weather, presence or absence of shadows or the like is changed, for example, when the brightness L is lower than the minimum brightness Ll, the electronic shutter control circuit 27 increases the shutter time by one step and conversely, when it is higher than the maximum brightness Lh, the shutter time is decreased by one step. Thereby, the shutter time of CCD 1 in the CCD control circuit 20 is controlled in multi steps from 1/60 to 1/10000 second such that the AGC control is always established, that is, the AGC control voltage VAGC is in the range of Vl through Vh and the current shutter step is sent to the input I/F 10 of the face image processing unit b as a shutter signal SS.

Further, the AGC control voltage VAGC corresponding to the image average brightness L is sent to the A/D converter 11 as a voltage signal VAGC through an amplifying circuit 23 and a buffer 24.

Incidentally, although a detailed explanation has been omitted in Embodiment 1, the illumination control is performed as follows when the external environment is in the dark state.

In FIG. 1 CPU 15 reads the brightness/darkness signal of the illumination sensor 7 from the input I/F 10 and the shutter signal SS from the electronic shutter control circuit 27 and reads the AGC control voltage VAGC corresponding to the image average brightness from the A/D converter 11, calculates a predetermined light emitting amount such that the AGC control is maintained in the control range when the shutter time is always 1/60 second in case where the external environment is determined to be in the dark state by the brightness/darkness signal and turns on the near infrared light source 6 by sending the illumination control signal from the output I/F 14 to the illumination control circuit 5.

Or, in case where the external environment is determined to be in the dark state by the brightness/darkness signal, although not shown, a control signal is sent from CPU 15 to the electronic shutter control circuit 27 via the output I/F 14 and turns on the near infrared ray light source 6 after fixing the shutter time to 1/60 second which is more preferable.

Now, the image signal processing circuit 2 is operated as mentioned above and therefore, the illuminance sensor 7 is omitted by using the above-mentioned operation.

For example, when the shutter speed becomes the minimum value of 1/60 second, the value of the AGC control voltage VAGC cannot be controlled to the target control voltage of the AGC control voltage and the deviation is magnified, it is a state in which the image storing time for receiving light is maximized and the target control voltage cannot be reached even if the provided image signal is amplified at maximum. Therefore, in this case the external environment can be determined as in the dark state.

Further, the determination of the bright state of the external environment can be performed when the shutter speed is shorter than 1/60 second. That is, this is a state wherein the AGC control voltage VAGC can be equalized to the target control voltage even if the image storing time is shorter than 1/60 second and therefore, the external environment can be regarded as sufficiently bright.

Further, as another method of determining the bright state, a state wherein the shutter speed is 1/60 second and the near infrared ray light source 6 is not turned on may be determined as the bright state.

That is, it is stated that the near infrared light source 6 is made illuminate by an arbitrary light emitting amount when the shutter speed is 1/60 second and the AGC control voltage VAGC does not reach the target control voltage. However, as mentioned above the state wherein the shutter speed is 1/60 second and the near infrared ray light source 6 is not turned on, is a state wherein the AGC control voltage VAGC can be equalized to the target voltage even if the near infrared ray light source 6 is not turned on and accordingly, the external environment can be determined as in the sufficiently bright state.

Therefore, the effect similar to that in Embodiment 1 is provided also in Embodiment 2 and a special sensor determining the brightness such as the illuminance sensor 7 is not necessary.

EMBODIMENT 3

Embodiment 3 is concerning a face image taking device removing the influence caused by the reflection by spectacles of a driver whereby a simplified face image taking device is provided without a brightness/darkness detecting means.

That is, in Embodiment 3 a brightness/darkness detecting means is not used and when eyes are not detected in step ST31 in FIG. 2, the near infrared light source 6 is turned on while omitting step ST32. As a result the near infrared ray is always irradiated when the eyes of a driver cannot be detected irrespective of the state of the external environment.

Now, in the above-mentioned Embodiments the near infrared ray light source 6 is excited so far as the eyes of a driver cannot be detected in the bright state of the day time and such a control is not performed in the dark state such as in the nighttime. However, a similar control is performed in Embodiment 3 even in the dark state as in the nighttime.

In other words, in the above-mentioned Embodiments the brightness/darkness state is detected and therefore, in case where a driver looks aside in the dark state the near infrared ray is not irradiated on the driver for removing the influence of the reflection by the spectacle lenses. By contrast there is a drawback in Embodiment 3 wherein the near infrared ray is irradiated if the eyes are not detected even in the dark state with no concern of the reflection by the spectacle lenses.

However, the device can be downsized, simplified and made inexpensive by the above-mentioned construction.

Therefore, according to Embodiment 3 it is possible to provide a simplified face image taking device receiving no influence of the reflection by the spectacle lenses.

EMBODIMENT 4

Embodiment 4 is a modified example of Embodiment 1 wherein the near infrared ray is irradiated on the face of a driver when the eyes cannot be detected and the spectacle frames are detected by determining that it is a state wherein the eyes cannot be detected due to the surface reflection by the spectacle lenses.

Figure 12:
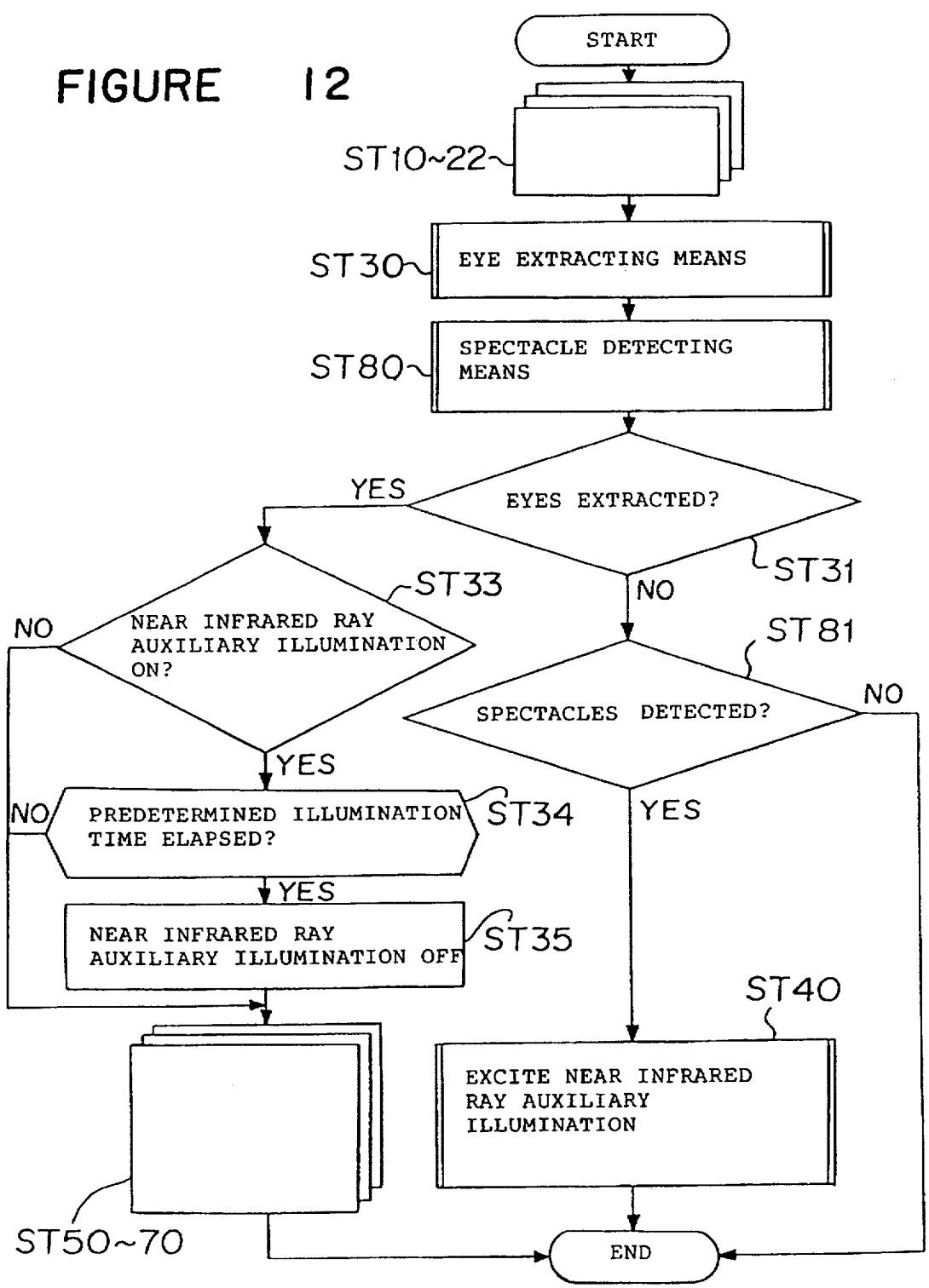
FIG. 12 is a flowchart in detecting a state of a driver of Embodiment 4.
Figure 13:
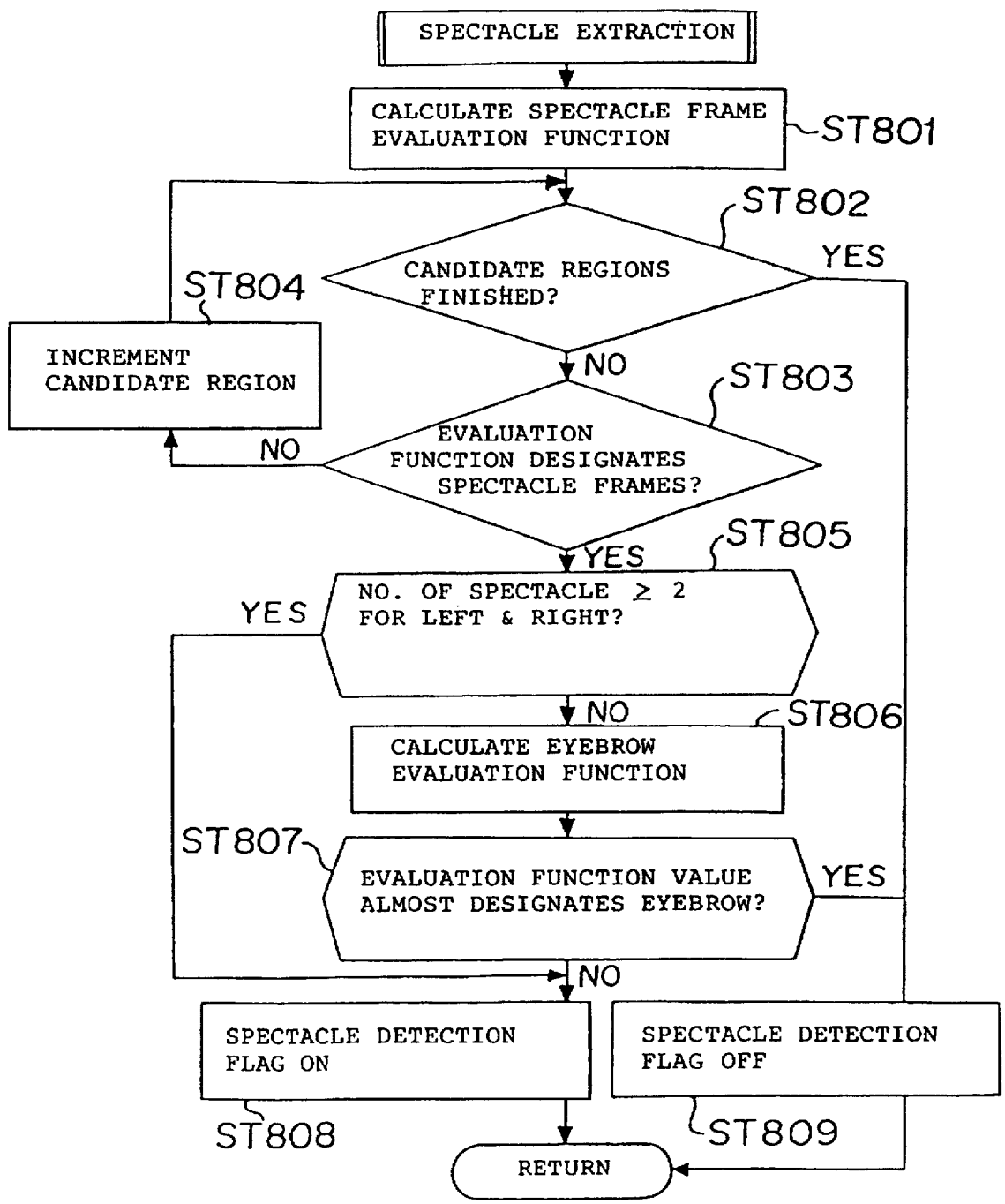
FIG. 13 is a flowchart in detecting spectacles in Embodiment 4.

FIG. 12 and FIG. 13 show Embodiment 4 of the present invention wherein FIG. 12 is a flowchart in detecting a state of a driver in Embodiment 4 and FIG. 13 is a flowchart in detecting spectacles. An explanation will be given of the Embodiment as follows in reference to FIGS. 12 and 13 and also FIGS. 1 and 9.

In FIG. 12, after performing the operation from step ST10 to the eye extracting means of step ST30, in a spectacle detecting means of step ST80 the operation determines whether the driver p wears the spectacle g.

A detailed explanation will be given later to a method of detecting spectacles by the spectacle detecting means by using a flowchart.

Next, in step ST31 the eye detection flag is investigated. When the eye detecting flag is OFF, successively in step ST81 a spectacle detection flag is investigated. When the spectacle detection flag is ON, the driver wears spectacles and also the eye cannot be detected. Determining that the cause by which the eyes are not extracted is the surface reflection by the spectacle lenses, in step ST40 the illumination control signal for removing the spectacle reflection is sent from the output I/F 14 to the illumination control circuit 5 by which the near infrared ray light source 6 is turned on.

Further, in case where the eye detection flag is ON in step ST31, steps 33 through 70 are performed as in Embodiment 1.

Now, an explanation will be given of the operation of the spectacle detecting means.

In detecting the spectacles firstly in step ST801 of FIG. 13 a spectacle frame evaluation function is calculated by using the X-axis histograms SUMX of the candidate regions 204 in the above-mentioned Embodiment 1. As shown in FIG. 9 SUMX of the spectacle frame shows an approximately flat characteristic as in the eyebrow and accordingly, the dispersion of the deviation (SUMXMAX–SUMX) is far smaller than that of the eyes. Further, a width EAW of the candidate region corresponding to the spectacle frame is normally a little longer than that of the eyebrow. The spectacle frame evaluation function is determined con sidering these characteristics. Next, in step ST802 the operation determines whether there are the candidate regions 204 other than the one identified as corresponding to the eye in step ST30. When there are the candidate regions 204, the operation determines whether each of the candidate regions 204 is corresponding to the spectacle frame based on the spectacle frame evaluation function in step ST803. When the operation determines that it is not corresponding to the spectacle frame, the operation increments the candidate region 204 in step ST804 and performs a similar operation with regard to the next one of the candidate regions. When there is no candidate region 204 to be determined in step ST802, the operation makes the spectacle detection flag OFF in step ST809 and the processing returns to the main routine.

Next, in step ST805 the operation investigates the number of the candidate regions 204 which have been determined as corresponding to the spectacle frames in the left and right candidate existing regions 202 in step ST802. When the number is two or more for each of the left and right candidate existing regions, the operation makes the spectacle detection flag ON in step ST808 by determining that either one of the two determined spectacle frames is the true spectacle frame. When the number of the candidate regions which have been determined as corresponding to the spectacle frame in each of the candidate existing regions 202 is one or zero, the operation calculates the eyebrow evaluating function using the above-mentioned SUMX and the above-mentioned EAW etc. of the candidate region 204 in step ST806. In step ST807 the operation determines whether the eyebrow evaluation function of the candidate region 204 is in a predetermined range, makes the spectacle detection flag ON in step ST808 similarly only in case where the eyebrow evaluation function is not in the predetermined range and when it is in the predetermined range, the operation makes the spectacle detection flag OFF in step ST809 as there is a possibility that the candidate region is corresponding to the eyebrow and the processing returns to the main routine.

In this way it is possible to determine whether the driver wears spectacles or not.

Accordingly, the effect similar to that in Embodiment 1 is provided in this embodiment. Further, by recognizing the presence of the spectacles it is possible to turn on firmly the near infrared light source 6 such that the eyes can be recognized on the image only in case where the eyes are considered to be invisible due to the reflection by the spectacle lenses by which the eyes can firmly be detected and the hour average power consumption can be reduced.

EMBODIMENT 5

Conventionally, there has been provided a near infrared ray illuminating means for a dark state to compensate for deficiency in illuminance when external environment is in a dark state.

By contrast in the above-mentioned embodiments the near infrared ray light source 6 for removing influence of reflection by spectacle lenses is provided to firmly detect eyes of a driver. The near infrared ray light source 6 is used not only as the near infrared ray illuminating means for removing influence of reflection by spectacle lenses but also as the near infrared ray illuminating means for a dark state by changing the control program of the illumination control circuit 5.

Meanwhile, there is a considerable difference between a light emitting amount of an infrared ray for extracting eyes from an image of a face in the dark state and a light emitting amount of an infrared ray for removing influence of reflection by spectacles in the daytime. Therefore, when the both functions are provided, power is wasted since an infrared ray having a light emitting amount more than necessary is irradiated in the dark state.

Therefore, in Embodiment 5 the hour average power consumption is reduced by separately functioning the both.

Figure 14:
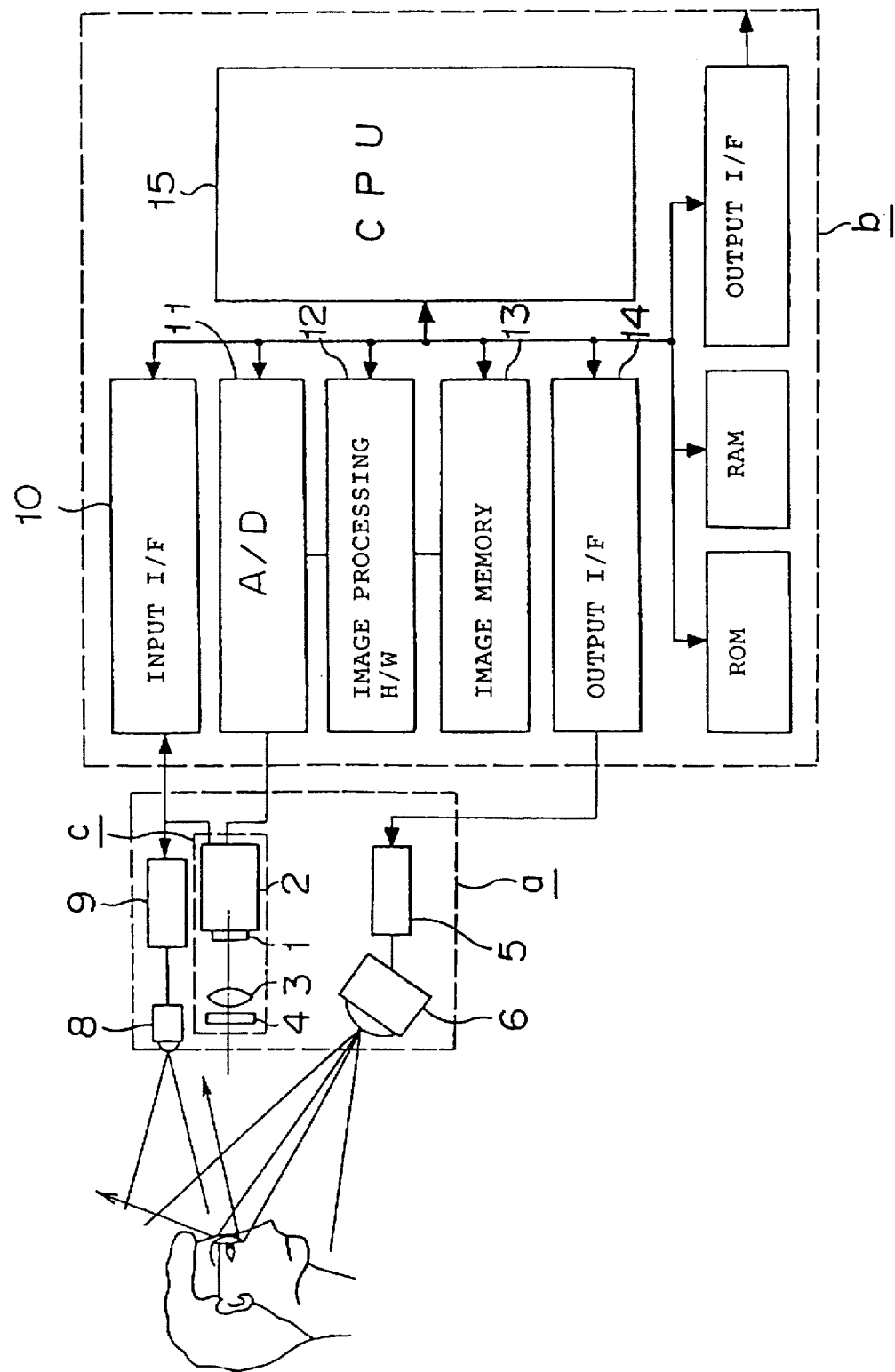
FIG. 14 is a structural view of a driver's state detecting device including a face image taking device of Embodiment 5.
Figure 15:
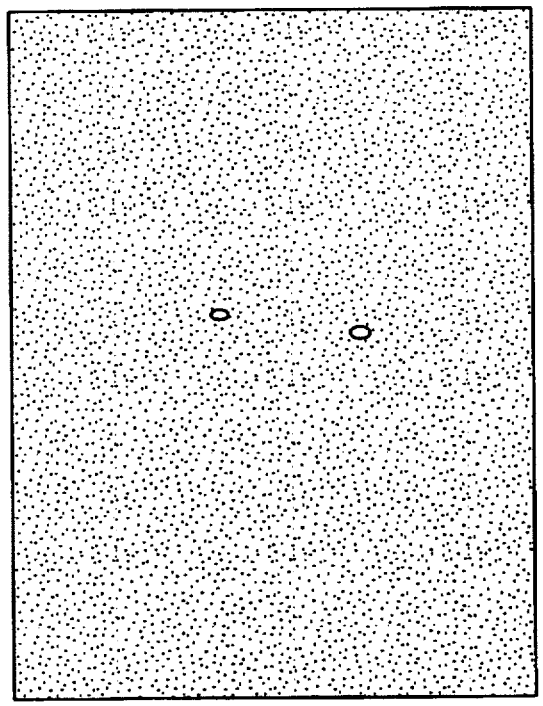
FIG. 15 shows an example of an image of a face in a dark state.

FIG. 14 and FIG. 15 show Embodiment 5 wherein FIG. 14 is a structural view of a driver's state detecting device including a face image taking device and FIG. 15 shows an example of an image of a face in a dark state.

In FIG. 14 numeral 8 designates a coaxial near infrared ray light source arranged proximate to the camera unit such that a radiating optical axis of a near infrared ray is approximately in parallel with and proximate to a photographing optical axis of the camera unit. In this example there is shown a case wherein a near infrared LED having a total light output as small as about 10 mW or less and a central wavelength of about 900 nm is used. Numeral 9 designates a LED control circuit to which the shutter signal SS and the AGC control voltage VAGC of the image signal processing circuit 2 as shown in FIG. 10 are connected. The shutter signal SS is connected to the input I/F 10, the image signal output VOUT and the AGC control voltage VAGC are connected to the A/D converter 11 and the illuminance sensor 7 is not used.

Now, an explanation will be given of the operation.

When the external environment becomes dark and the brightness on the operator p is lowered, the AGC control circuit 22 and the electronic shutter control circuit 27 in FIG. 10 are operated and the shutter time is increased. When the shutter time becomes 1/60 second and the AGC control voltage is a predetermined value or less, the LED control circuit 9 turns on the near infrared ray LED 8 by determining the dark state. The radiating optical axis of the near infrared ray LED 8 is approximately coaxial with the photographing optical axis of the camera unit c and therefore, it is possible to clearly photograph only pupils of the driver p as shown in FIG. 15. The pupils have a property of reflecting incident light almost in the same direction and therefore, the brightness thereof in the coaxial illuminating state is conspicuously larger than that of other portions of a face and accordingly, only the pupils are distinctly photographed as shown in FIG. 15 even with the near infrared ray LED 8 of which beam is so weak that the feature of a face cannot be photographed as an image. At this occasion the average brightness is not enhanced at all since the brightness on the image is magnified only at the pupils having a size of approximately 7 through 8 mm at maximum. Although not illustrated, in such a dark state only the pair of pupils of the driver p are binarized as white level in step ST20 of the main routine. Therefore, CPU omits step ST21 in FIG. 2 and receives the binary image of the image memory 13, detects the pair of pupils based on an algorithm different from that in the bright state and the evaluation function in the eye extracting means of step ST30 and detects blinking since the pupils are hidden by eyelids in blinking thereby similarly performing the dozing determination.

In this Embodiment as in the above-mentioned Embodiments, the bright state is determined in case where the shutter speed is 1/60 second or shorter or in case where the shutter speed is 1/60 second and the AGC control voltage VAGC is the predetermined value or more.

Further, in case where the eyes are not detected in the image in the bright state, the near infrared ray light source 6 is turned on as in Embodiment 1. Or, in case where the spectacles are detected and the eyes are not detected in the image in the bright state, the near infrared ray light source 6 is turned on as in Embodiment 4.

Therefore, according to Embodiment 5 the effect similar to the above-mentioned embodiments is achieved and it is possible to further reduce the hour average power consumption of that of the total photographing device by separating the near infrared ray LED 8 having a low power consumption that is normally used in the dark state from the near infrared ray light source 6 for removing influence of reflection by spectacle lenses, and provide the near infrared ray light source 6 with a long life by limiting the use of the near infrared ray light source 6.

Further, in Embodiment 5 the pupils of the driver p are photographed by the near infrared ray LED 8 in the dark state. However, the pupils may be photographed by using other infrared ray light source arranged approximately to the camera unit c such that the radiating optical axis thereof is approximately in parallel with and proximate to the photographing optical axis of the camera unit c.

EMBODIMENT 6

In Embodiment 6 an optical filter is arranged on the optical axis of a camera by which eyes can firmly be detected even if reflection by spectacle lenses is caused.

Figure 16:
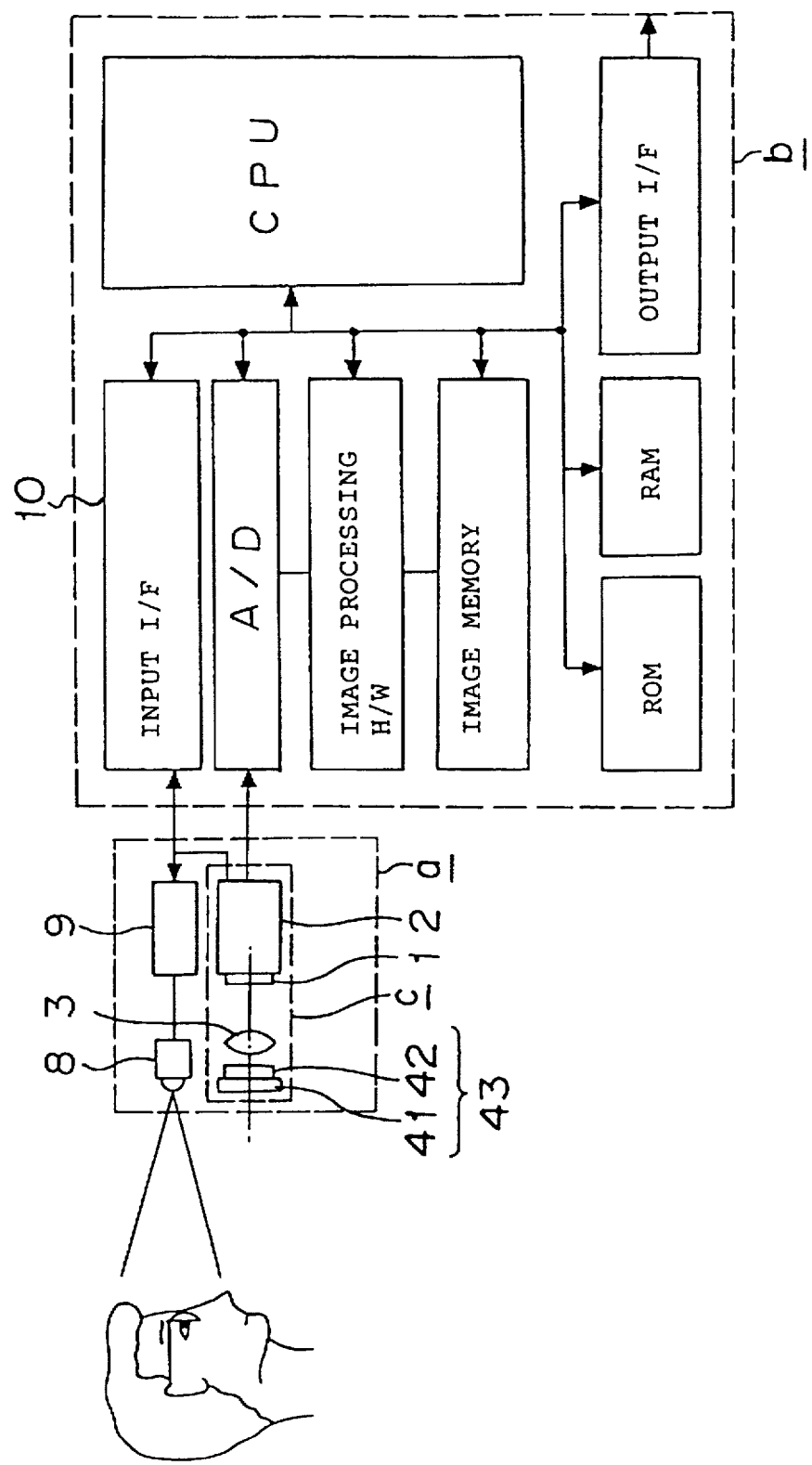
FIG. 16 is a structural view of a driver's state detecting device including a face image taking device in Embodiment 6.
Figure 17:
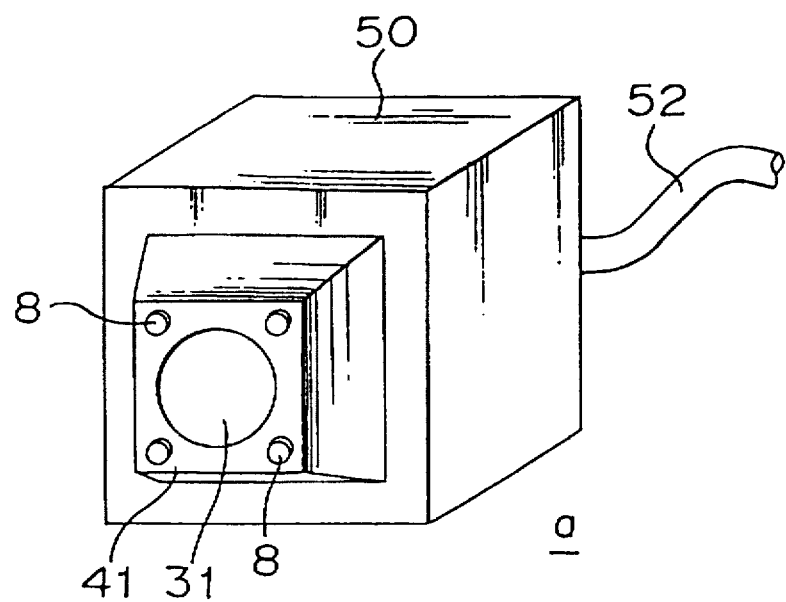
FIG. 17 is a perspective view of an outlook of a image taking unit a in Embodiment 6.
Figure 18:
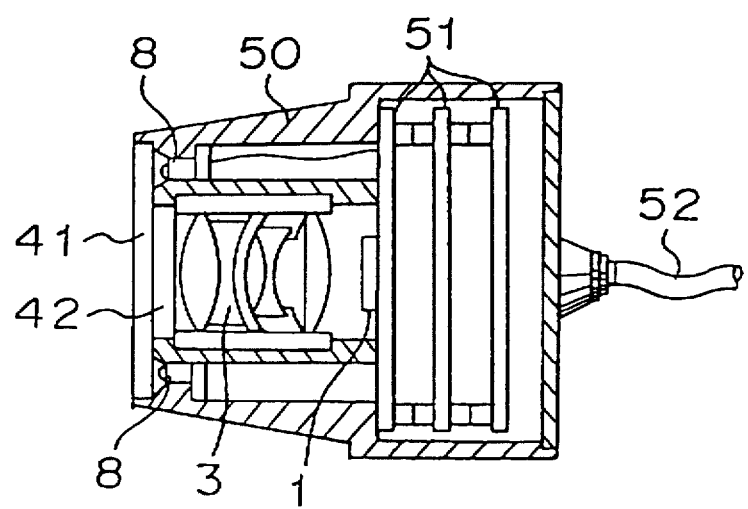
FIG. 18 is a sectional view of the image taking unit a of Embodiment 6.
Figure 19:
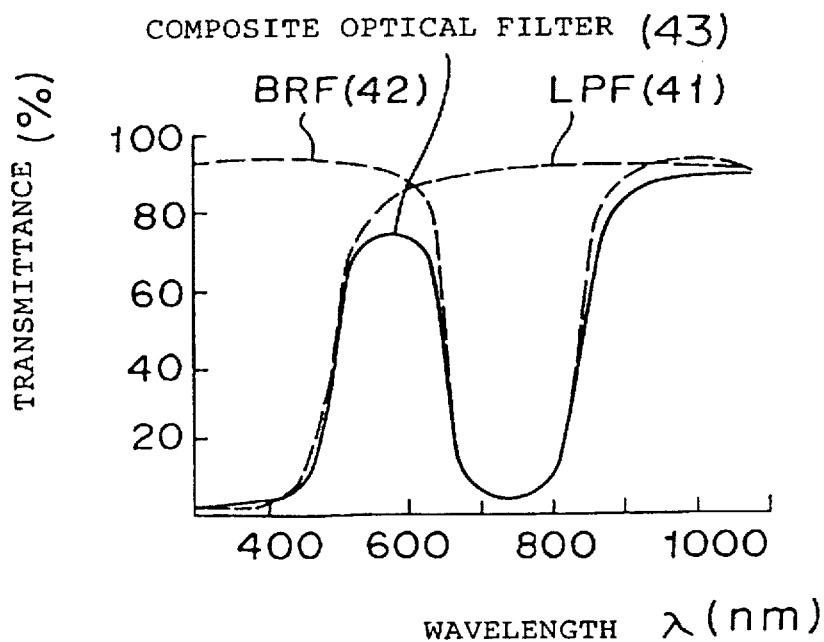
FIG. 19 is a characteristic diagram of a spectroscopic transmittance of a composite optical filter.

FIG. 16 through FIG. 19 show Embodiment 6 where FIG. 16 is a structural view of a driver's state detecting device including a face image taking device of Embodiment 6, FIG. 17 is a perspective view of an outlook of an image taking unit a, FIG. 18 is a sectional view of the image taking unit a and FIG. 19 illustrates spectroscopic transmittance characteristic diagram of a composite optical filter.

In FIGS. 16 through 18 numerals 41 and 42 are optical filters overlappingly arranged on the photographing optical axis of the camera unit c in front of the image taking lens 3, numeral 50 designates a housing supporting CCD 1, the image taking lens 3, the optical filters 41 and 42 and the like and also the near infrared ray LED 8 is supported in the housing. Numeral 51 designates printed circuit boards in which CCD 1, the image signal processing circuit 2 and the LED control circuit 9 are arranged and numeral 52 designates an output lead of the image taking unit a. With regard to the near infrared ray LEDs 8, the LEDs having a central wavelength of approximately 900 nm as in Embodiment 5 are symmetrically provided at four locations on the rear side of the optical filters such that the LEDs are proximate to an opening 31 of the lens as shown in FIG. 17 in which the photographing optical axis of the camera unit c is approximately in parallel with the radiating optical axes of the near infrared ray.

However, the near infrared LEDs 8 may be arranged with no intermediary of the optical filter 41 different from those in FIG. 17.

Next, an explanation will be given of the optical filters.

As shown in FIG. 19 the optical filter 41 is a long wavelength transmitting filter (LPF) as is illustrated by a dotted line in the figure. Here is shown an example using a LPF having a wavelength of approximately 500 nm at transmittance of 50% by which light having a wavelength of 500 nm or more including visible light and infrared ray light is transmitted. Further, the optical filter 42 is a band removing filter (BRF). Here is shown an example using a BRF having wavelengths of 650 nm and 850 at transmittance of 50% and removing a wavelength band of 650 to 850 nm situated between visible light and near infrared ray. BRF 42 uses a dielectric multi-layer filter wherein dielectric films in multi-layers are laminated on a transparent optical substrate made of glass, plastic or the like. LPF 41 uses a similar dielectric multi-layer filter or an inexpensive absorption type filter wherein colorants are diffused in the above-mentioned transparent optical substrate.

LPF 41 and BRF 42 overlap as shown in FIG. 18 and constitute a composite optical filter 43 having high values of the spectroscopic transmittance at the vicinity of a median of the wavelength band of approximately 400 to 700 nm wherein the transmittance of a coating of spectacle lenses is high and at the surrounding of the central wavelength of the near infrared ray LED 8 that is used in photographing in the dark state.

Accordingly, the composite optical filter 43 is provided with two transmitting bands wherein a first transmitting band ranges 400 through 700 nm and a second transmitting band ranges 850 nm or more.

By using the above-mentioned composite optical filter 43 the pupils of the driver p are photographed by turning on the infrared ray LEDs 8 in the dark state as in Embodiment 5 utilizing the high spectroscopic transmittance thereof at surrounding of the central wavelength of the near infrared ray LEDs 8 whereby a state of the driver, that is, dozing etc. is detected.

Further, in the bright state the image of the face of the driver p is taken by the above-mentioned two components of the wavelength regions in external light utilizing the high spectroscopic transmittances in the ranges of the wavelength of 500 to 650 nm and 850 nm or more.

Incidentally, in case where the conventional visible light cut filter 4 is used, the spectroscopic reflectance of the spectacle lenses in the light removing region of the filter 4 is low and conversely the spectroscopic reflectance of the spectacle lens in the transmitting regions of the filter 4 is high. Therefore, the value of K indicating the visibility of the eye is small and the eyes cannot be photographed at all as shown in FIG. 28.

By contrast the composite optical filter 43 of this embodiment is provided with a high transmittance in a region in which the spectroscopic reflectance of the visible light wavelength of the spectacle lens is low and therefore, the diffused reflecting luminous flux ΦiT from the eyes in the visible light region is efficiently received by the CCD 1 and the above-mentioned ratio of K is enhanced by which the eyes can distinctly be photographed as shown in FIG. 6.

Accordingly, this embodiment has an advantage wherein the eyes can distinctly be photographed without using a special illumination for removing the reflection even if there is the surface reflection by the spectacle lenses by taking an image of the face of the driver p wearing the spectacle g by the components of the transmitting wavelength bands of the visible light of the solar ray and the near infrared ray in the bright state by using the composite optical filter 43 having pass bands both in the visible light wavelength range wherein the transmittance of the spectacle lenses is high and the near infrared wavelength range corresponding to the near infrared ray illumination for taking the image of the driver p in the dark state.

EMBODIMENT 7

Embodiment 7 is a modified example of Embodiment 6 wherein a more distinct image of a face is provided than that in Embodiment 6.

Figure 20:
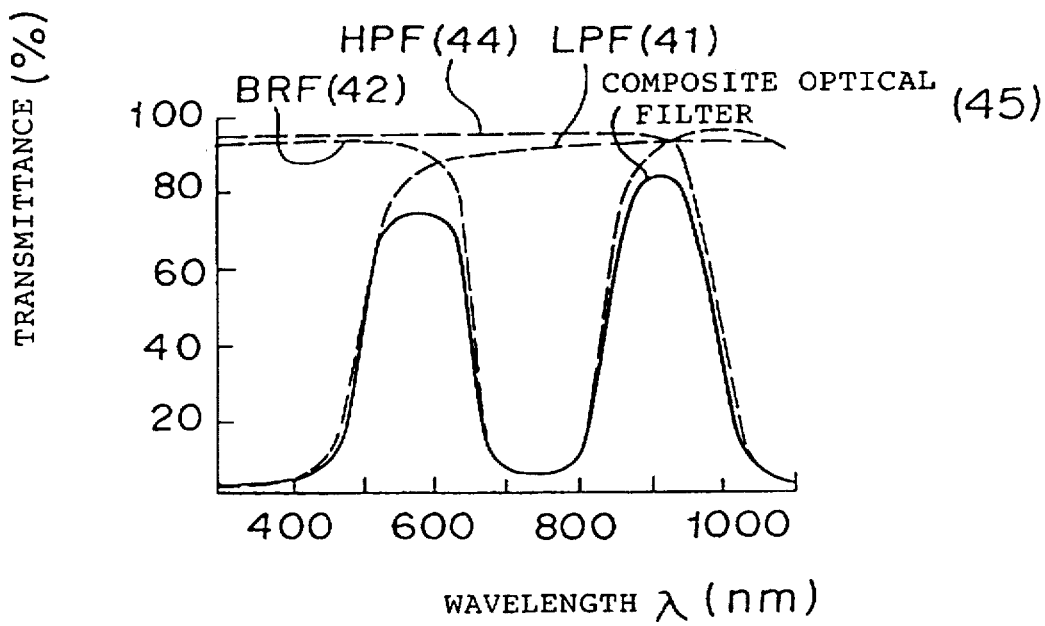
FIG. 20 is a characteristic diagram of a spectroscopic transmittance of a composite optical filter of Embodiment 7.

FIG. 20 shows a spectroscopic transmittance characteristic diagram of a composite optical filter 45 in Embodiment 7. The composite optical filter 43 of FIG. 19 is further overlapped by a short wavelength transmitting filter (HPF) having a wavelength of approximately 950 nm at transmittance of 50% to constitute a composite optical filter limiting transmitting wavelength bands only at the vicinity of the median of the wavelength band of approximately 400 to 700 nm wherein the transmittance of the coating of the spectacle lens is high and at the vicinity of the central wavelength of the near infrared ray LED 8 which is used in photographing in the dark state.

Further, it is preferable to use a dielectric multi-layer film in HPF 44 as in BRF 42. The composite optical filter 45 is arranged in front of the image taking lens of the camera unit c as in Embodiment 6, the pupils of the driver p are photographed by turning on the near infrared ray LED 8 in a dark state and the image of the face of the driver p is taken only by the wavelength components of external light of 500 to 650 nm and 850 to 950 nm in the bright state.

Here, the first transmitting band is in the wavelength region of 500 to 650 nm and the second transmitting band is in the wavelength region of 850 to 950 nm.

When the composite optical filter 45 is used, light only in the two wavelength bands, that is, the wavelength band of illumination of near infrared ray used in photographing in the dark state and the visible wavelength band including the diffused reflecting luminous flux ΦiT from the eyes in the visible light region and therefore, disturbance light in the other wavelength regions can be removed. Accordingly, it is possible to remove large reflection caused in a wavelength region of 700 nm or more, the eyes can be photographed more distinctly even if there is the surface reflection of the spectacle lens and the photographing S/N ratio of the driver p in the dark state can be improved since surrounding noise light does not invade the camera because light in the wavelength region other than necessary is cut.

EMBODIMENT 8

Embodiment 8 is concerning simplification of a face image taking device.

In the above-mentioned Embodiments 6 and 7 there are separate filters of LPF 41, BRF 42 and HPF 44. However, it is possible to form the composite optical filter 43 having the spectroscopic transmittance characteristic as shown by the bold line in FIG. 19 by a single sheet of substrate when, for example, BRF 42 is produced by laminating a dielectric multi-layer film on one face of the substrate of the absorption type LPF 41, or forming LPF 41 on one face of a transparent substrate and BRF 42 on the other face thereof by laminating dielectric multi-layer films on both faces thereof.

Further, the composite optical filter 45 having the spectroscopic transmittance characteristic shown by the bold line in FIG. 20 can be formed by one substrate by forming BRF 42 on one face of a substrate of the absorption type LPF 41 and HPF 44 on the other face thereof by laminating dielectric multi-layer films on both faces of the substrate.

Therefore, according to these methods, the composite optical filter 45 can be thinned and manufactured at a low cost and there causes no such a troublesome problem as positioning of a plurality of filters.

EMBODIMENT 9

Embodiment 9 is concerning combination of the above-mentioned Embodiments wherein, even if the surface reflection by the spectacle lens is comparatively strong, the influence can be dispensed with.

Although not illustrated, the influence of the reflection by the spectacle lens can further be reduced by replacing the optical filter 4 at the camera unit c as shown in Embodiment 1 or Embodiment 5 by the composite optical filter 43 or the composite optical filter 45 as shown in the above-mentioned Embodiments 6 and 7.

That is, firstly the influence of the surface reflection by the spectacle lenses is reduced by photographing the driver p by using the camera unit c in which the above-mentioned composite optical filter 43 or the composite optical filter 45 is used. Further, as in Embodiment 1 or Embodiment 5 the near infrared ray light source 6 is turned on by sending the illumination control signal for removing the spectacle reflection to the illumination control circuit 5 via the output I/F 14 in case where the external environment or the vicinity of the face of the driver p is in the bright state or the spectacles the driver p are detected and still the eyes cannot be detected.

According to this embodiment even in a state wherein the surface reflection by the optical lens is extremely strong as in a case in which white cloud, white wall or the like is reflected by the optical lens under clear weather, the eyes can distinctly be photographed by firmly removing the influence of the lens reflection by turning on the near infrared ray light source 6.

Further, the eyes can distinctly be photographed by the composite optical filter 43 or the composite optical filter 45 when there is normally caused surface reflection by the spectacle lenses and therefore, occurrence of a state in which the eyes cannot be detected becomes small by which the frequency of use of the near infrared ray light source 6 in the bright state is reduced and the life can further be prolonged.

EMBODIMENT 10

In Embodiment 10 two optical filters are used by switching them by which the eye can distinctly be detected without providing the near infrared ray light source 6 for removing the influence of the reflection of the spectacle lenses.

Figure 21:
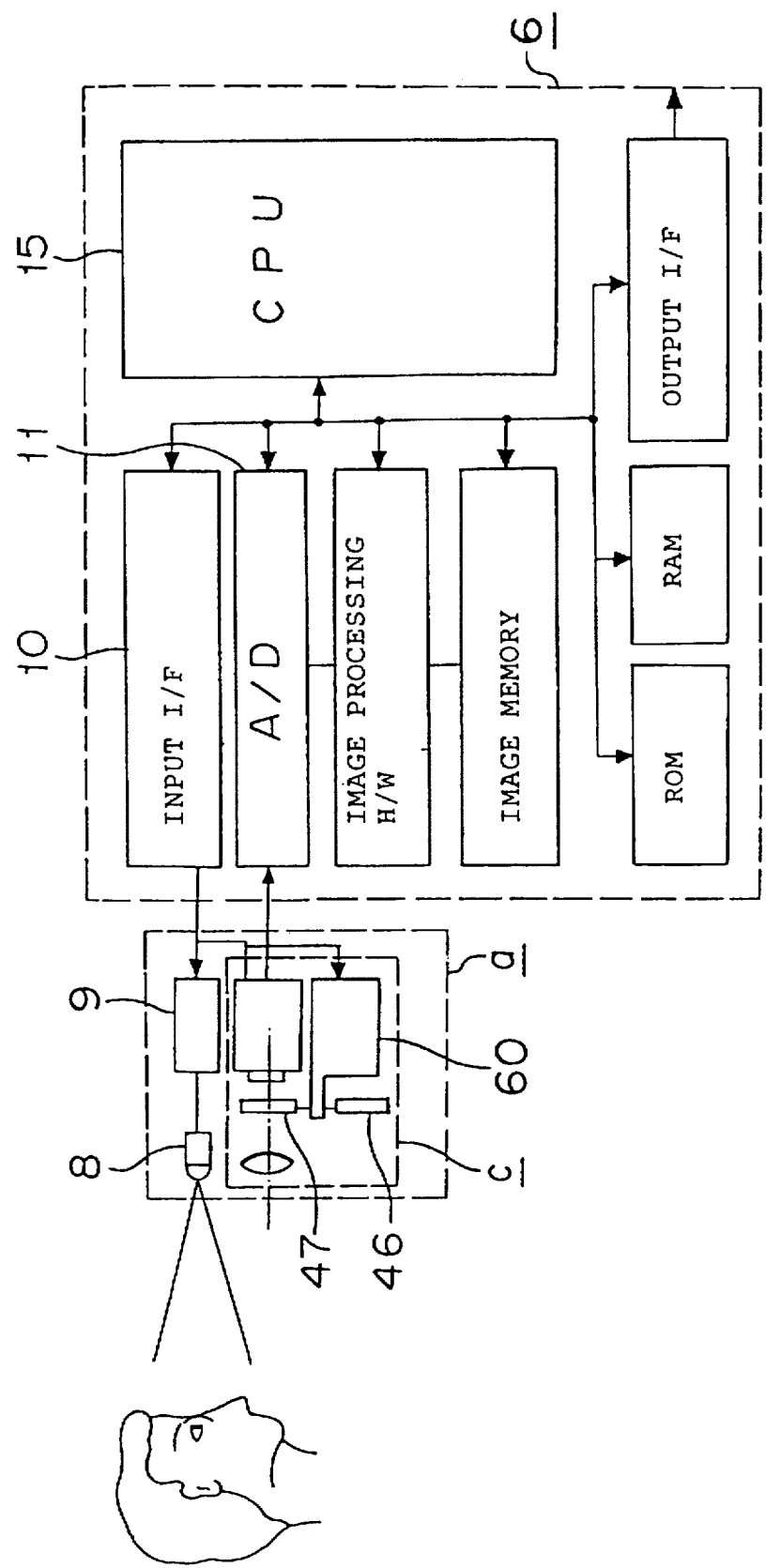
FIG. 21 is a structural view of a driver's state detecting device including a face image taking device in Embodiment 10.
Figure 22:
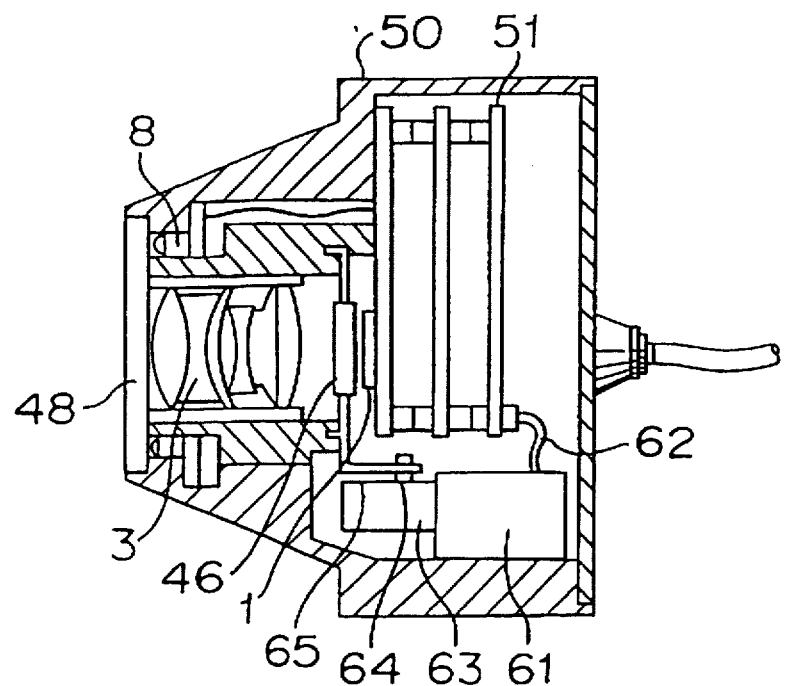
FIG. 22 is a sectional view of an image taking unit a of Embodiment 10.
Figure 23:
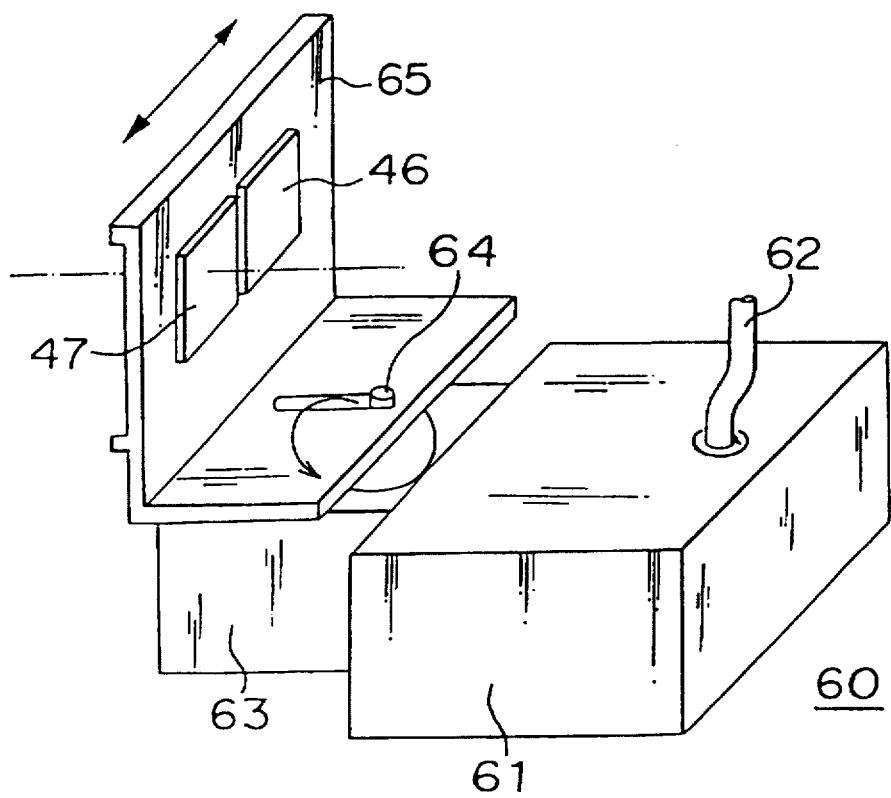
FIG. 23 is a perspective view of a filter interchanging unit of Embodiment 10.
Figure 24:
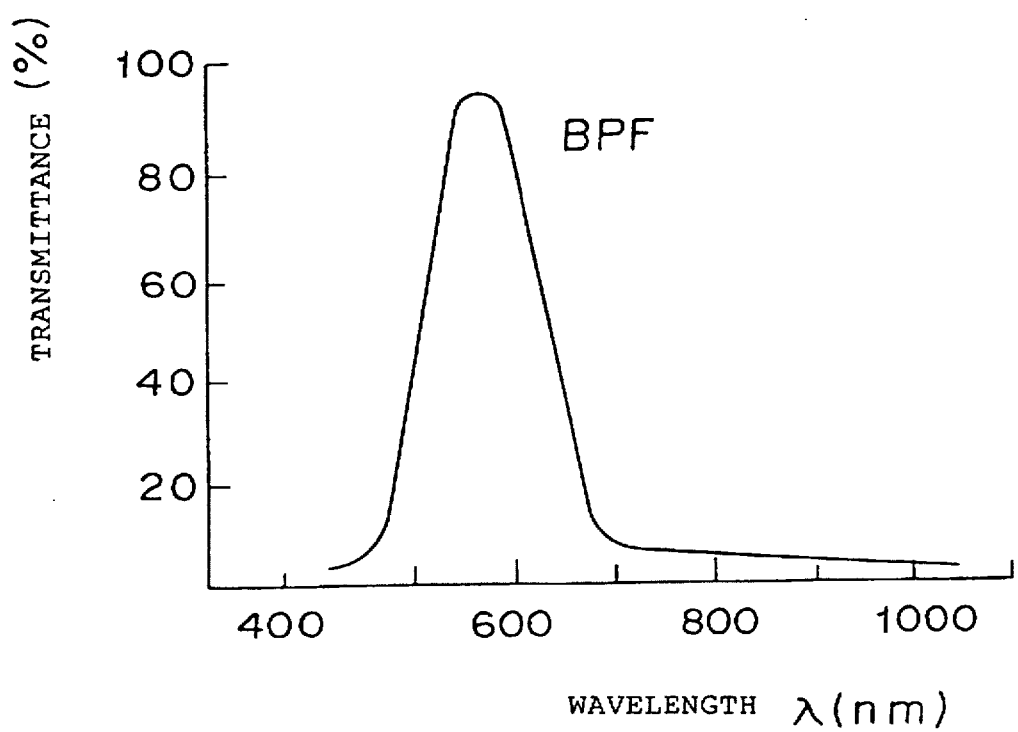
FIG. 24 is a characteristic diagram of a spectroscopic transmittance of one optical filter of Embodiment 10.
Figure 25:
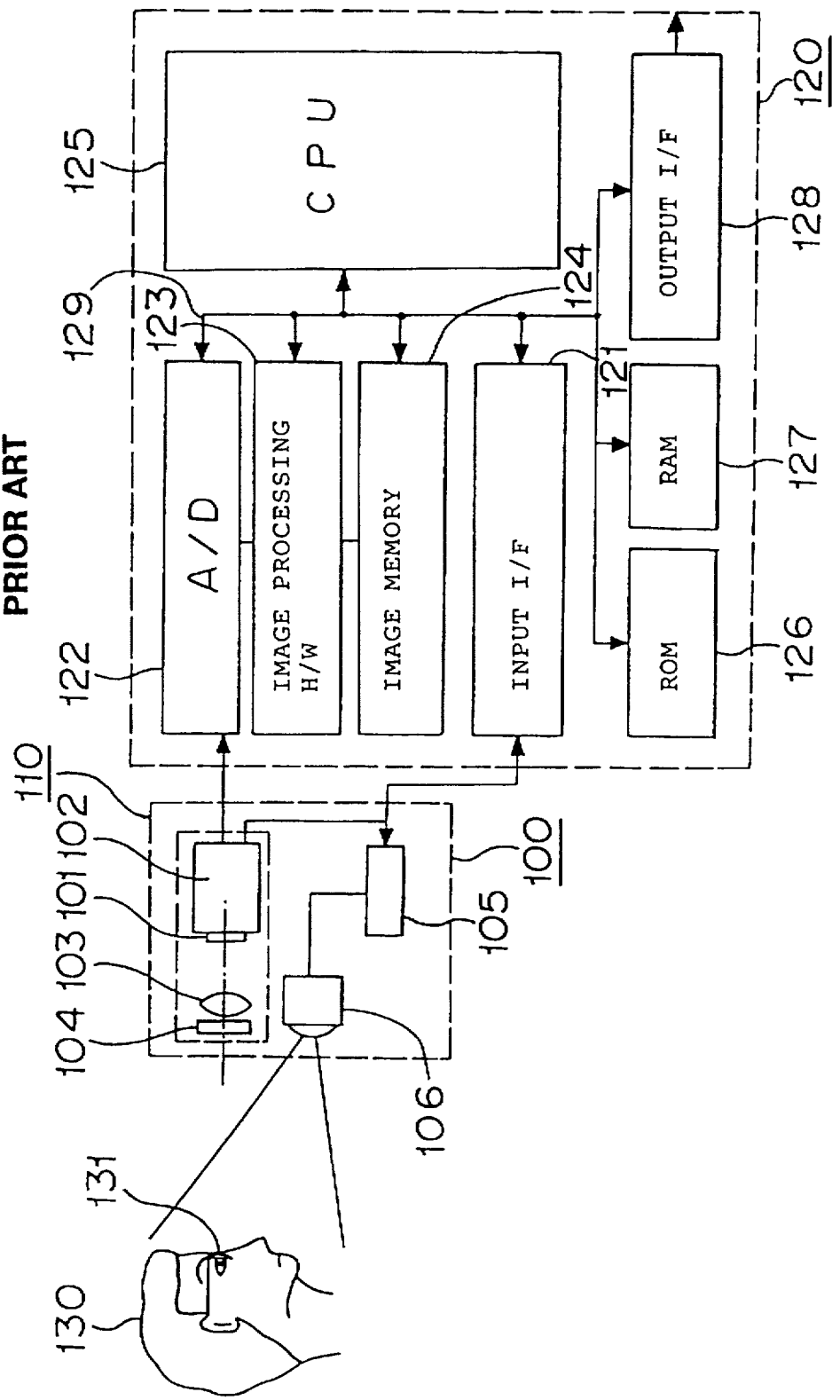
FIG. 25 is a structural view of a driver's state detecting device including a conventional face image taking device.
Figure 26:
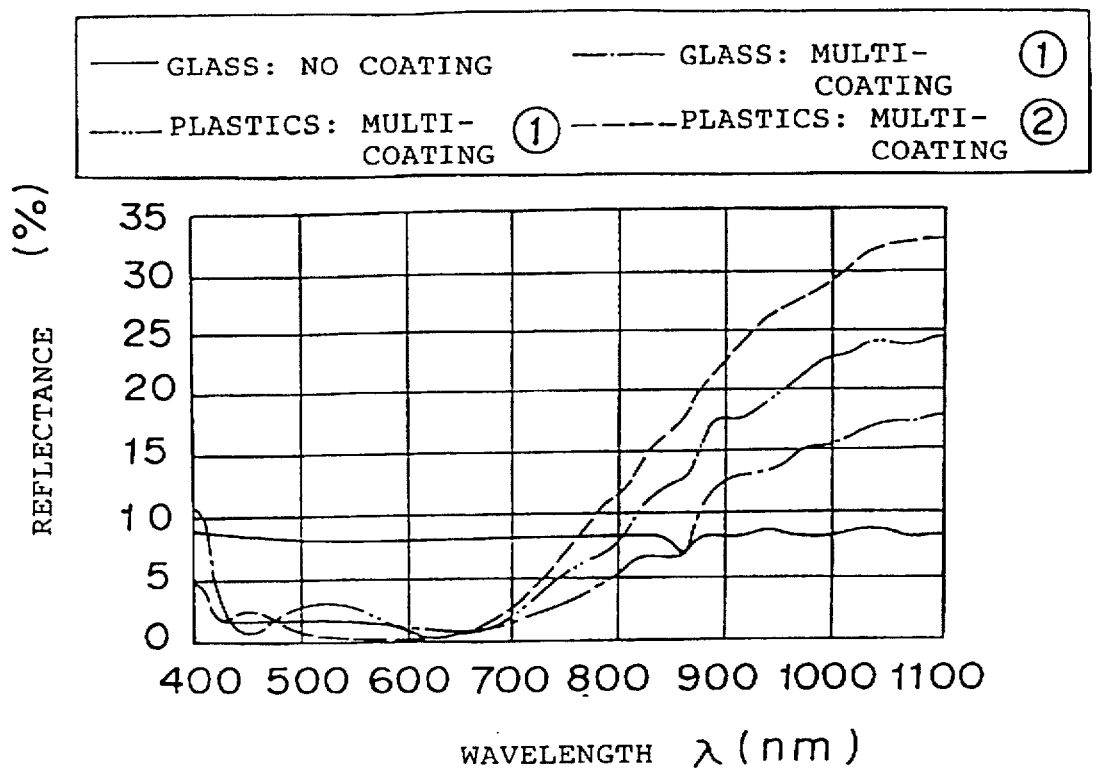
FIG. 26 illustrates characteristic diagrams of spectroscopic reflectances of various spectacle lenses.

FIG. 21 through FIG. 24 show Embodiment 10 wherein FIG. 21 is a structural view of a driver's state detecting device including a face image taking device of Embodiment 10. FIG. 22 is a sectional view of an image taking unit a, FIG. 23 is a perspective view of a film interchanging unit and FIG. 24 is a spectroscopic transmittance characteristic diagram of an optical filter 46 for one side.

In FIGS. 21 through 23 numeral 46 designates a first optical filter having a pass band only in a visible light region in which the transmittance of the coating of the spectacle lens is high. As shown in FIG. 24 the filter is a band pass filter (BPF) having wavelengths of 500 nm and 650 nm at transmittance of 50%. Numeral 47 designates a second optical filter wherein the transmitting wavelength is in conformity with the wavelength region of the near infrared ray light source for illuminating the driver p in the dark state. The second optical filter may use a normal visible light cut filter in case where, for example, the near infrared ray LED 8 having the central wavelength of 900 nm is used as the near infrared ray light source as in the above-mentioned Embodiment 5. However, when BPF having a half value width of approximately 100 nm centering on the wavelength of 900 nm is used, disturbance light components other than the illuminating light can be removed which is advantageous. Further, the visible light region in which the transmittance of the coating of the spectacle lens is high is the first pass band and the wavelength region of the near infrared ray light source for illuminating the driver p in a dark state is the second pas band.

Numeral 60 designates a film interchanging means for switching the first optical filter 46 and the second optical filter 47 and the film interchanging means is incorporated in a housing 50 of the image taking unit a. Although the first optical filter 46 and the second optical filter 47 may be arranged on the front side of the lens 3, in this embodiment they are arranged on the rear side of the lens 3 by which the filter interchanging means 60 is downsized and chromatic aberration of the lens 3 is corrected by changing the effective focal length of the lens 3 by changing the thickness and material, that is, the refractive index of the filter substrate in accordance with the transmitting wavelength band. Numeral 48 designates a transparent protective member such as glass that is coated by a reflection preventive coating.

The filter interchanging means 60 is constituted by a motor 61 generating a drive force for interchanging the filters, the lead 62 for issuing signals to the motor 61, a gear box 63 for reducing the rotational speed of the motor 61, a rotational cam plate 64 having a protruded roller pin and pivoted by receiving a rotational force from the gear box 63 and a filter supporting plate 65 in a L-shape supporting the two filters on one face thereof and having an elongated hole for inserting the roller pin on the other face thereof.

An explanation will be given of the operation of Embodiment 10.

Firstly, in resetting the device the first optical filter 46 for passing visible light is arranged on the photographing axis and the image of the face of the driver p is photographed by the component light in the transmitting wavelength region of the filter by passing it through the first optical filter 46. In this case the transmitting wavelength region of the first optical filter 46 is in conformity with the wavelength region in which the spectroscopic reflectance of the spectacle lens is low and therefore, even if there is the surface reflection of the lens of spectacle g worn by the driver p, the incidence of the reflected light on the camera is hampered by the first optical filter 46. Meanwhile, the wavelength component in the transmitting band of the first optical filter 46 in the diffused reflection luminous flux ΦiT from the eyes is incident on the camera without being hampered by the first optical filter 46 by which the eyes can distinctly be photographed.

When the external environment becomes dark and the average brightness of the image of the face of the driver p is lowered, the image signal processing circuit 2 performs the AGC control and controls the shutter to the open side. Under such a state the brightness/darkness determination is performed as in Embodiment 2, and in case where the dark state is determined, the first filter is switched to the second optical filter 47.

When the brightness/darkness signal from the image signal processing circuit 2 on the printed wiring boards 51 outputs a signal showing the dark state, CPU 15 issues a drive signal to the motor 61 via the lead 62 and the motor 61 is rotated. The rotational number of the motor 61 is reduced by the gear box 62 connected to the motor 61 and the rotational cam plate 64 is rotated by a half rotation. The rotational motion is converted into a linear motion by the elongated hole of the filter supporting plate 65 and the roller pin of the rotational cam plate 64 that is inserted into the elongated hole and the linear motion moves the filter supporting plate 65 orthogonal to the photographing axis by which the first optical filter 46 is switched to the second optical filter 47.

Further, at this occasion, the near infrared ray LED 8 is turned on, the face of the driver is illuminated and the pupils are photographed.

Conversely, when the external environment is changed from the dark state to the bright state, that is, when the time changes from night to morning, solar ray is added to the near infrared ray of the near infrared ray LED 8. Therefore, the second optical filter 47 passes the illumination light of the near infrared LED 8 and the component of the near infrared ray of the solar ray. Thereby, the average brightness of the image of the face of the driver p is enhanced, the image signal processing circuit 2 determines that the dark state is changed to the bright state based on the enhancement of the brightness and outputs a signal showing the bright state to CPU 10. Receiving the signal showing the bright state CPU 15 rotates the motor 61 in a direction reverse to the above-mentioned direction, switches the second optical filter 47 to the first optical filter 46 and turns off the near infrared ray LED 8.

In this embodiment, the driver p is photographed by using the visible light wavelength region which is not influenced by the surface reflection of the spectacle lenses in the bright state and therefore, the eyes can distinctly be photographed without using a special illumination for removing the reflection even if there is the reflection by the spectacle lenses, the driver p is photographed only by the wavelength region of the near infrared light source illuminating the driver p in the dark state and therefore, disturbance light is removed and the photographing S/N ratio of the driver p can be improved.

EMBODIMENT 11

Embodiment 11 extremely reduce the influence of the surface reflection by the spectacle lenses by combining Embodiment 1 with Embodiment 10.

That is, Embodiment 11 is provided with the camera unit c having the filter interchanging means 60 shown in the above-mentioned Embodiment 10, the brightness/darkness detecting means such as the illuminance sensor 7 explained in Embodiment 1, the illumination control circuit 5 and the near infrared ray light source 6 for removing the influence of the reflection by the spectacle lenses.

Therefore, in the bright state the image of the face driver p is photographed by switching the filter to the first optical filter 46 having the pass band only in the visible light region wherein the transmittance of the coating of the spectacle lenses is high by which the influence of the surface reflection by the lens is firstly reduced and the near infrared ray light source 6 is turned on by sending the illumination control signal for removing the reflection of spectacles to the illumination control circuit 5 via the output I/F 14 in case where the external environment or the vicinity of the face of the driver p is in the bright state or the spectacle of the driver p is detected and still the eyes cannot be detected, as in Embodiment 1 or Embodiment 5.

In this embodiment even in case where the surface reflection by the lenses is extremely strong as in Embodiment 9, the eyes can distinctly be photographed by turning on the near infrared ray light source 6 by which the influence of the lens reflection can firmly be removed and the eyes can distinctly be photographed only by the first optical filter 46 in the normally caused lens reflection. Therefore, the frequency of use of the near infrared ray light source in the bright state is reduced and the life can further be prolonged.

Although the pupils of the driver p are photographed by the near infrared ray LED 8 in the dark state in the above-mentioned Embodiment 6 through Embodiment 11, the face of the driver may be illuminated and photographed by using the near infrared region of a light source such as a halogen lamp or a xenon lamp, or the near infrared light source 6 in which a number of near infrared LEDs are assembled as in Embodiment 1.

Further, although the face image taking devices for detecting dozing or the like of a driver of a vehicle has been shown in the respective above-mentioned embodiments, they can naturally be utilized as face image taking devices utilized in a person's state detecting device generally detecting a state of a person to be detected by detecting eyes of the person to be detected by image-processing an image of the face of the person to be detected.

The present invention achieves the following effects owing to the above-mentioned structures.

According to the face image taking device of this invention the face of a person to be detected is illuminated by exciting the infrared ray illuminating means when the eye detecting means does not detect the eyes of the person to be detected and therefore, the influence by the reflection by spectacles worn by the driver can be reduced.

According to the face image taking device of this invention the face of the person to be detected is illuminated by exciting the infrared ray illuminating means in case where the brightness/darkness detecting means detects the bright state and further the eye detecting means does not detect the eyes of the person to be detected and therefore, power consumption can be reduced.

According to the face image taking device of this invention the bright state or the dark state is determined based on whether the brightness of the image including the face of the person to be detected that is photographed by the two-dimensional image taking means is a predetermined brightness or more and therefore, the structure of the device can be simplified.

According to the face image taking device of this invention the infrared ray illuminating means is once stopped after a predetermined time has elapsed since the infrared ray illuminating means was excited and therefore, the infrared ray illuminating means can be excited when necessary.

According to the face image taking device of this invention the face of the person to be detected is illuminated by exciting the infrared ray illuminating means in case where the spectacle detecting means detects the spectacles and the eye detecting means does not detect the eyes of the person to be detected and therefore, power consumption can be reduced.

According to the face image taking device of this invention the device is provided with the infrared ray illuminating means for the dark state which illuminates the face of the person to be detected by the infrared ray passing through the optical filter when the brightness/darkness detecting means detects the dark state and the infrared ray illuminating means for the dark state and the infrared ray illuminating means excited when the eye detecting means does not detect the eyes of the person to be detected separately function and therefore, power consumption can be reduced.

According to the face image taking device of this invention the image of the face of the person to be detected is photographed by passing the visible light in the predetermined wavelength region and the infrared ray having a predetermined wavelength or more through the filter and therefore, the influence of the reflection by the spectacles worn by the driver can be reduced by a simple structure.

According to the face image taking device of this invention the image of the face of the person to be detected is photographed only by the visible light in the predetermined wavelength region and the infrared ray having the predetermined wavelength range and therefore, a more distinct image can be provided.

According to the face image taking device of this invention the image of the face of the person to be detected is photographed by the visible light in the predetermined wavelength region and the infrared ray having the predetermined wavelength or more, and the face of the person to be detected is illuminated by exciting the infrared ray illuminating means in case where the eyes cannot be detected by the image of the face, and therefore, even in a case where the reflection by the spectacles worn by the driver is comparatively strong, the influence can be reduced.

According to the face image taking device of this invention the first optical filter is arranged on the optical axis of the two-dimensional image taking means when the brightness/darkness detecting means detects the bright state and the second optical filter is arranged on the optical axis of the two-dimensional image taking means when the brightness/darkness detecting means detects the dark state and therefore, the eyes can distinctly be detected and the influence of the reflection by the spectacles worn by the driver can be reduced.

What is claimed is:

1. A face image taking device comprising:
   a two-dimensional image taking means for taking an image of a predetermined region including a face of a person to be detected;
   an optical filter having a pass band passing at least an infrared ray in a predetermined wavelength region and arranged on an optical axis of the two-dimensional image taking means;
   an eye detecting means for detecting eyes of the person to be detected based on the image of the face of the person to be detected which has been taken by the two-dimensional image taking means, said eye detecting means outputting a signal indicative of whether at least one eye has been detected;
   an infrared ray illuminating means for illuminating at least the face of the person to be detected by an infrared ray which has passed through the optical filter, said infrared ray illuminating means being arranged such that an angle made by the optical axis of the two-dimensional image taking means and an optical axis of the infrared ray is a predetermined angle or more; and
   an exciting means for exciting the infrared ray illuminating means based on said signal output by said eye detecting means indicating a failure to detect an eye of said person.

2. The face image taking device according to claim 1, wherein the exciting means stops the infrared ray illuminating means when a predetermined period of time has elapsed since the infrared ray illuminating means was excited.

3. The face image taking device according to claim 1, further comprising a spectacle detecting means for detecting presence or absence of spectacle worn by the person to be detected; and wherein the exciting means excites the infrared ray illuminating means in case where the spectacle detecting means detects spectacles and the eye detecting means does not detect the eyes of the person to be detected.

4. The face image taking device according to claim 1, wherein said signal is independent of the brightness in the vicinity of said person.

5. The face image taking device according to claim 1, further comprising a brightness/darkness detecting means for detecting either one of a bright state and a dark state at a surrounding of the person to be detected or at a vicinity of the face by detecting a brightness of the surrounding of the person to be detected or the vicinity of the face; and wherein the exciting means excites the infrared ray illuminating means in case where the brightness/darkness detecting means detects the bright state and the eye detecting means does not detect the eyes of the person to be detected.

6. The face image taking device according to claim 5, wherein the brightness/darkness detecting means determines either one of the bright state and the dark state based on whether a brightness of an image including the face of the person to be detected which has been taken by the two-dimensional image taking means is a predetermined brightness or more.

7. The face image taking device according to claim 5, further comprising a second infrared ray illuminating means for the dark state for illuminating the face of the person to be detected by an infrared ray which has passed through the optical filter when the brightness/darkness detecting means detects the dark state, said second infrared ray illuminating means for the dark state being provided separately from the infrared ray illuminating means excited when the eye detecting means does not detect the eyes of the person to be detected.

8. A face image taking device comprising:

a two-dimensional image taking means for taking an image of a predetermined region including a face of a person to be detected; and an optical filter having a first pass band passing a visible light in a predetermined wavelength range and a second pass band passing an infrared ray having a predetermined wavelength or more and arranged on an optical axis of the two-dimensional image taking means.

9. The face image taking device according to claim 8, wherein the second pass band of the optical filter passes only an infrared ray in a predetermined wavelength range.

10. A face image taking device comprising:

a two-dimensional image taking means for taking an image of a predetermined region including a face of a person to be detected;

an optical filter having a first pass band passing a visible light in a predetermined wavelength range and a second pass band passing an infrared ray having a predetermined wavelength or more and arranged on an optical axis of the two-dimensional image taking means;

an eye detecting means for detecting eyes of a person to be detected based on an image of the face of the person to be detected which has been taken by the two-dimensional image taking means, said eye detecting means outputting a signal indicative of whether at least one eye has been detected;

an infrared ray illuminating means for illuminating at least the face of the person to be detected by an infrared ray which has passed through the optical filter, said infrared ray illuminating means being arranged such that an angle made by an optical axis of the two-dimensional image taking means and an optical axis of the infrared ray is a predetermined angle or more; and an exciting means for exciting the infrared ray illuminating means based on said signal output by said eye detecting means indicating a failure to detect an eye of said person.

11. The face image taking device according to claim 8, further comprising a first optical filter having a first pass band and a second optical filter having a second pass band both constituting the optical filter;

a brightness/darkness detecting means for detecting either one of a bright state and a dark state at a surrounding of the person to be detected or at a vicinity of the face by detecting a brightness of the surrounding of the person to be detected or the vicinity of the face; and a filter interchanging means for disposing the first optical filter on an optical axis of the two-dimensional image taking means when the brightness/darkness detecting means detects the bright state and disposing the second optical filter on the optical axis of the two-dimensional image taking means when the brightness/darkness detecting means detects the dark state.

12. The face image taking device according to claim 10, further comprising a first optical filter having a first pass band and a second optical filter having a second pass band both constituting the optical filter;

a brightness/darkness detecting means for detecting either one of a bright state and a dark state at a surrounding of the person to be detected or at a vicinity of the face by detecting a brightness of the surrounding of the person to be detected or the vicinity of the face; and a filter interchanging means for disposing the first optical filter on an optical axis of the two-dimensional image taking means when the brightness/darkness detecting means detects the bright state and disposing the second optical filter on the optical axis of the two-dimensional image taking means when the brightness/darkness detecting means detects the dark state.

13. A face image taking device comprising:

a two-dimensional image receiver operable to receive an image of a predetermined region including a face of a person to be detected;

an optical filter having a pass band passing at least an infrared ray in a predetermined wavelength region and arranged on an optical axis of the two-dimensional image receiver;

an eye detector operable to detect an eye of the person to be detected based on the image of the face of the person to be detected which has been taken by the two-dimensional image receiver, said eye detector outputting a signal to said image taking device indicative of whether at least one eye has been detected, said signal based at least in part on information besides the brightness of the area in the vicinity of said person;

an infrared ray illuminator operable to illuminate the face of the person to be detected by an infrared ray which has passed through the optical filter, said infrared ray illuminator being arranged such that an angle made by the optical axis of the two-dimensional image receiver and an optical axis of the infrared ray is a predetermined angle or more; and an exciter operable to excite the infrared ray illuminator based on said signal output by said eye detector indicating a failure to detect an eye of the person to be detected.

14. The face image taking device according to claim 13, wherein the exciter once stops the infrared ray illuminator when a predetermined period of time has elapsed since the infrared ray illuminator was excited.

15. The face image taking device according to claim 13, further comprising a spectacle detector operable to detect the presence or absence of a spectacle worn by the person to be detected; and wherein the exciter excites the infrared ray illuminator if the spectacle detector detects spectacles and the eye detector does not detect the eyes of the person to be detected.

16. The face image taking device according to claim 13, wherein said signal is independent of the brightness in the vicinity of said person.

17. The face image taking device according to claim 13, further comprising a brightness/darkness detector operable to detect either one of a bright state and a dark state at a surrounding of the person to be detected or at a vicinity of the face by detecting a brightness of the surrounding of the person to be detected or the vicinity of the face; and wherein the exciter excites the infrared ray illuminator if the brightness/darkness detector detects the bright state and the eye detector does not detect an eye of the person to be detected.

18. The face image taking device according to claim 17, wherein the brightness/darkness detector determines either one of the bright state and the dark state based on whether a brightness of an image including the face of the person to be detected which has been taken by the two-dimensional image receiver is a predetermined brightness or more.

19. The face image taking device according to claim 13, further comprising a second infrared ray illuminator operable to illuminate the face of the person to be detected in the dark state by an infrared ray which has passed through the optical filter when the brightness/darkness detector detects the dark state, said second infrared ray illuminator being provided separately from the infrared ray illuminator excited when the eye detector does not detect the eyes of the person to be detected.

20. A face image taking device comprising:

a two-dimensional image receiver operable to receive an image of a predetermined region including a face of a person to be detected; and an optical filter having a first pass band passing a visible light in a predetermined wavelength range and a second pass band passing an infrared ray having a predetermined wavelength or more and arranged on an optical axis of the two-dimensional image receiver.

21. The face image taking device according to claim 20, wherein the second pass band of the optical filter passes only an infrared ray in a predetermined wavelength range.

22. The face image taking device according to claim 20, further comprising a first optical filter having a first pass band and a second optical filter having a second pass band both constituting the optical filter;

a brightness/darkness detector operable to detect either one of a bright state and a dark state at a surrounding of the person to be detected or at a vicinity of the face by detecting a brightness of the surrounding of the person to be detected or the vicinity of the face; and a filter interchanger operable to dispose the first optical filter on an optical axis of the two-dimensional image receiver when the brightness/darkness detector detects the bright state and disposing the second optical filter on the optical axis of the two-dimensional image receiver when the brightness/darkness detector detects the dark state.

23. A face image taking device comprising:

a two-dimensional image receiver operable to receive an image of a predetermined region including a face of a person to be detected;

an optical filter having a first pass band passing a visible light in a predetermined wavelength range and a second pass band passing an infrared ray having a predetermined wavelength or more and arranged on an optical axis of the two-dimensional image receiver;

an eye detector operable to detect an eye of a person to be detected based on an image of the face of the person to be detected which has been taken by the two-dimensional image receiver, said eye detector outputting a signal indicative of whether at least one eye has been detected, said signal based at least in part on information besides the brightness of the area in the vicinity of said person;

an infrared ray illuminator operable to illuminate the face of the person to be detected by an infrared ray which has passed through the optical filter, said infrared ray illuminator being arranged such that an angle made by an optical axis of the two-dimensional image receiver and an optical axis of the infrared ray is a predetermined angle or more; and an exciter operable to excite the infrared ray illuminator based on said signal output by said eye detector indicating a failure to detect an eye of the person to be detected.

24. The face image taking device according to claim 23, further comprising a first optical filter having a first pass band and a second optical filter having a second pass band both constituting the optical filter;

a brightness/darkness detector operable to detect either one of a bright state and a dark state at a surrounding of the person to be detected or at a vicinity of the face by detecting a brightness of the surrounding of the person to be detected or the vicinity of the face; and a filter interchanger operable to dispose the first optical filter on an optical axis of the two-dimensional image receiver when the brightness/darkness detector detects the bright state and dispose the second optical filter on the optical axis of the two-dimensional image receiver when the brightness/darkness detector detects the dark state.

* * * * *